US008907066B2

(12) United States Patent
Lo et al.

(10) Patent No.: US 8,907,066 B2
(45) Date of Patent: Dec. 9, 2014

(54) ANTIBODY FUSION PROTEINS WITH A MODIFIED FCRN BINDING SITE

(75) Inventors: Kin-Ming Lo, Lexington, MA (US); Pascal A. Stein, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 598 days.

(21) Appl. No.: 12/763,662

(22) Filed: Apr. 20, 2010

(65) Prior Publication Data

US 2010/0272720 A1    Oct. 28, 2010

Related U.S. Application Data

(60) Provisional application No. 61/171,650, filed on Apr. 22, 2009.

(51) Int. Cl.
| C12P 21/08 | (2006.01) |
| C07K 16/46 | (2006.01) |
| C07K 14/565 | (2006.01) |
| A61K 38/00 | (2006.01) |
| A61K 38/21 | (2006.01) |
| A61K 39/00 | (2006.01) |
| C07K 16/00 | (2006.01) |

(52) U.S. Cl.
CPC .......... *C07K 16/00* (2013.01); *C07K 2319/30* (2013.01); *C07K 2317/53* (2013.01); *C07K 2319/02* (2013.01); *C07K 2317/52* (2013.01)
USPC ................... 530/387.3; 530/351; 530/388.22; 424/85.6; 424/134.1; 514/1.1

(58) Field of Classification Search
None
See application file for complete search history.

(56) References Cited

U.S. PATENT DOCUMENTS

| 4,469,797 A | 9/1984 | Albarella |
| 4,737,462 A | 4/1988 | Mark et al. |
| 5,019,368 A | 5/1991 | Epstein et al. |
| 5,349,053 A | 9/1994 | Landolfi |
| 5,480,981 A | 1/1996 | Goodwin et al. |
| 5,514,582 A | 5/1996 | Capon et al. |
| 5,541,087 A | 7/1996 | Lo et al. |
| 5,601,819 A | 2/1997 | Wong et al. |
| 5,609,846 A | 3/1997 | Goldenberg |
| 5,614,184 A | 3/1997 | Sytkowski et al. |
| 5,645,835 A | 7/1997 | Fell, Jr. et al. |
| 5,650,150 A | 7/1997 | Gillies |
| 5,679,543 A | 10/1997 | Lawlis |
| 5,709,859 A | 1/1998 | Aruffo et al. |
| 5,723,125 A | 3/1998 | Chang et al. |
| 5,726,044 A | 3/1998 | Lo et al. |
| 5,728,552 A | 3/1998 | Fujisawa et al. |
| 5,770,195 A | 6/1998 | Hudziak et al. |
| 5,795,779 A | 8/1998 | McCormick et al. |
| 5,827,516 A | 10/1998 | Urban et al. |
| 5,827,703 A | 10/1998 | Debs et al. |
| 5,843,423 A | 12/1998 | Lyman et al. |
| 5,908,626 A | 6/1999 | Chang et al. |
| 5,998,598 A | 12/1999 | Csaky et al. |
| 6,086,875 A | 7/2000 | Blumberg et al. |
| 6,100,387 A | 8/2000 | Herrmann et al. |
| 6,169,070 B1 | 1/2001 | Chen et al. |
| 6,335,176 B1 | 1/2002 | Inglese et al. |
| 6,444,792 B1 | 9/2002 | Gray et al. |
| 6,475,717 B1 | 11/2002 | Enssle et al. |
| 6,485,726 B1 | 11/2002 | Blumberg et al. |
| 6,500,641 B1 | 12/2002 | Chen et al. |
| 6,551,592 B2 | 4/2003 | Lindhofer et al. |
| 6,617,135 B1 | 9/2003 | Gillies et al. |
| 6,620,413 B1 | 9/2003 | DeSauvage et al. |
| 6,627,615 B1 | 9/2003 | Debs et al. |
| 6,646,113 B1 | 11/2003 | Dreyfuss et al. |
| 6,750,329 B1 | 6/2004 | Rosenblum et al. |
| 6,821,505 B2 * | 11/2004 | Ward .............................. 424/9.1 |
| 6,838,260 B2 | 1/2005 | Gillies et al. |
| 6,969,517 B2 | 11/2005 | Gillies et al. |
| 6,992,174 B2 | 1/2006 | Gillies et al. |
| 7,067,110 B1 | 6/2006 | Gillies et al. |
| 7,091,321 B2 | 8/2006 | Gillies et al. |
| 7,141,651 B2 | 11/2006 | Gillies et al. |
| 7,148,321 B2 | 12/2006 | Gillies et al. |

(Continued)

FOREIGN PATENT DOCUMENTS

| AU | 21725/88 A | 3/1989 |
| EP | 0237019 A2 | 9/1987 |
| EP | 0294703 A2 | 12/1988 |
| EP | 0308936 A2 | 3/1989 |
| EP | 0314317 A1 | 5/1989 |
| EP | 0318554 B1 | 6/1989 |
| EP | 0326120 A2 | 8/1989 |
| EP | 0350230 A2 | 1/1990 |
| EP | 0375562 A2 | 6/1990 |
| EP | 0396387 A2 | 11/1990 |

(Continued)

OTHER PUBLICATIONS

Skolnick and Fetrow. From genes to protein structure and function: novel applications of computational approaches in the genomic era. Trends in Biotechnology, 2000. vol. 18, pp. 34-39.*

(Continued)

*Primary Examiner* — Robert Landsman
*Assistant Examiner* — Bruce D Hissong
(74) *Attorney, Agent, or Firm* — Goodwin Procter LLP

(57) ABSTRACT

Disclosed are antibody fusion proteins with a modified FcRn binding site and nucleic acid molecules encoding them. The antibody fusion protein include two polypeptide chains, wherein the first polypeptide chain includes a biologically active molecule linked to at least a portion of an immunoglobulin constant region. The second polypeptide chain includes at least a portion of an immunoglobulin constant region. One of the polypeptide chains includes a mutation in the FcRn binding site that reduces binding to FcRn. Also disclosed are methods of producing the fusion proteins and methods of using the fusion proteins for treating diseases and conditions alleviated by the administration of the fusion proteins.

9 Claims, 17 Drawing Sheets

(56) References Cited

U.S. PATENT DOCUMENTS

| | | |
|---|---|---|
| 7,148,326 B2 | 12/2006 | Itoh |
| 7,169,904 B2 | 1/2007 | Gillies et al. |
| 7,186,804 B2 | 3/2007 | Gillies et al. |
| 7,211,253 B1 | 5/2007 | Way |
| 7,226,998 B2 | 6/2007 | Gillies et al. |
| 7,323,549 B2 | 1/2008 | Lauder et al. |
| 7,348,004 B2 | 3/2008 | Peters et al. |
| 7,381,795 B2 | 6/2008 | Carr et al. |
| 7,404,956 B2 | 7/2008 | Peters et al. |
| 7,432,357 B2 | 10/2008 | Gillies |
| 7,459,538 B2 | 12/2008 | Gillies et al. |
| 7,462,350 B2 | 12/2008 | Gillies et al. |
| 7,465,447 B2 | 12/2008 | Gillies et al. |
| 7,507,406 B2 | 3/2009 | Gillies et al. |
| 7,517,526 B2 | 4/2009 | Gillies et al. |
| 7,576,193 B2 | 8/2009 | Gillies et al. |
| 7,582,288 B2 | 9/2009 | Gillies et al. |
| 7,589,179 B2 | 9/2009 | Gillies et al. |
| 7,601,814 B2 | 10/2009 | Gillies et al. |
| 7,670,595 B2 | 3/2010 | Gillies et al. |
| 2001/0053539 A1 | 12/2001 | Lauffer et al. |
| 2002/0037558 A1 | 3/2002 | Lo et al. |
| 2002/0081664 A1 | 6/2002 | Lo et al. |
| 2002/0142374 A1 | 10/2002 | Gallo et al. |
| 2002/0146388 A1 | 10/2002 | Gillies |
| 2002/0147311 A1 | 10/2002 | Gillies et al. |
| 2002/0192222 A1 | 12/2002 | Blumberg et al. |
| 2002/0193570 A1 | 12/2002 | Gillies et al. |
| 2003/0003529 A1 | 1/2003 | Bayer |
| 2003/0012789 A1 | 1/2003 | Blumberg et al. |
| 2003/0044423 A1 | 3/2003 | Gillies et al. |
| 2003/0049227 A1 | 3/2003 | Gillies et al. |
| 2003/0105294 A1 | 6/2003 | Gillies et al. |
| 2003/0139365 A1 | 7/2003 | Lo et al. |
| 2003/0139575 A1 | 7/2003 | Gillies |
| 2003/0157054 A1 | 8/2003 | Gillies et al. |
| 2003/0166163 A1 | 9/2003 | Gillies |
| 2003/0166877 A1 | 9/2003 | Gillies et al. |
| 2004/0013640 A1 | 1/2004 | Zardi et al. |
| 2004/0033210 A1 | 2/2004 | Gillies |
| 2004/0043457 A1 | 3/2004 | Schumacher et al. |
| 2004/0053366 A1 | 3/2004 | Lo et al. |
| 2004/0072299 A1 | 4/2004 | Gillies et al. |
| 2004/0082039 A1 | 4/2004 | Gillies et al. |
| 2004/0180035 A1 | 9/2004 | Gillies |
| 2004/0180386 A1 | 9/2004 | Carr et al. |
| 2004/0203100 A1 | 10/2004 | Gillies et al. |
| 2005/0032174 A1 | 2/2005 | Peters et al. |
| 2005/0042729 A1 | 2/2005 | Lo et al. |
| 2005/0054052 A1 | 3/2005 | Carr et al. |
| 2005/0069521 A1 | 3/2005 | Gillies et al. |
| 2005/0137384 A1 | 6/2005 | Gillies et al. |
| 2005/0164352 A1 | 7/2005 | Lauder et al. |
| 2005/0192211 A1 | 9/2005 | Gillies et al. |
| 2005/0202021 A1 | 9/2005 | Gillies |
| 2005/0202538 A1 | 9/2005 | Gillies et al. |
| 2005/0244418 A1 | 11/2005 | Gillies et al. |
| 2005/0261229 A1 | 11/2005 | Gillies et al. |
| 2006/0025573 A1 | 2/2006 | Gillies et al. |
| 2006/0034836 A1 | 2/2006 | Gillies et al. |
| 2006/0141581 A1 | 6/2006 | Gillies et al. |
| 2006/0194952 A1 | 8/2006 | Gillies et al. |
| 2006/0228332 A1* | 10/2006 | Gillies et al. ............ 424/85.6 |
| 2006/0263856 A1 | 11/2006 | Gillies et al. |
| 2007/0036752 A1 | 2/2007 | Gillies et al. |
| 2007/0059282 A1 | 3/2007 | Gillies et al. |
| 2007/0104689 A1 | 5/2007 | Gillies et al. |
| 2007/0154453 A1 | 7/2007 | Webster et al. |
| 2007/0154473 A1 | 7/2007 | Super et al. |
| 2007/0172928 A1 | 7/2007 | Peters et al. |
| 2007/0178098 A1 | 8/2007 | Way et al. |
| 2007/0202103 A1 | 8/2007 | Gillies et al. |
| 2007/0258944 A1 | 11/2007 | Gillies et al. |
| 2007/0287170 A1 | 12/2007 | Davis et al. |
| 2008/0025947 A1 | 1/2008 | Gillies et al. |
| 2008/0311655 A1 | 12/2008 | Gillies et al. |
| 2009/0010875 A1 | 1/2009 | Lauder et al. |
| 2009/0043076 A1 | 2/2009 | Carr et al. |
| 2009/0088561 A1 | 4/2009 | Gillies et al. |
| 2009/0092607 A1 | 4/2009 | Gillies et al. |
| 2009/0098609 A1 | 4/2009 | Gillies et al. |
| 2009/0148441 A1 | 6/2009 | Gillies |
| 2009/0191154 A1 | 7/2009 | Gillies et al. |
| 2009/0264627 A1 | 10/2009 | Gillies et al. |
| 2010/0015089 A1 | 1/2010 | Gillies et al. |
| 2010/0016562 A1 | 1/2010 | Gillies et al. |
| 2010/0029499 A1 | 2/2010 | Davis |
| 2010/0068175 A1 | 3/2010 | Gillies et al. |
| 2010/0174056 A1 | 7/2010 | Gillies et al. |

FOREIGN PATENT DOCUMENTS

| | | |
|---|---|---|
| EP | 0428596 B1 | 5/1991 |
| EP | 0439095 A2 | 7/1991 |
| EP | 0511747 A1 | 11/1992 |
| EP | 0601043 B1 | 6/1994 |
| EP | 0706799 A2 | 4/1996 |
| EP | 1088888 A1 | 4/2001 |
| JP | 63267278 A | 11/1988 |
| JP | 63267296 A | 11/1988 |
| WO | WO-86/01533 A1 | 3/1986 |
| WO | WO-88/00052 A1 | 1/1988 |
| WO | WO-89/02922 A1 | 4/1989 |
| WO | WO-91/00360 A1 | 1/1991 |
| WO | WO-91/08298 A2 | 6/1991 |
| WO | WO-91/13166 A1 | 9/1991 |
| WO | WO-91/14438 A1 | 10/1991 |
| WO | WO-92/02240 A2 | 2/1992 |
| WO | WO-92/08495 A1 | 5/1992 |
| WO | WO-92/08801 A1 | 5/1992 |
| WO | WO-92/10755 A1 | 6/1992 |
| WO | WO-92/16562 A1 | 10/1992 |
| WO | WO-93/03157 A1 | 2/1993 |
| WO | WO-94/25609 A1 | 11/1994 |
| WO | WO-95/05468 A1 | 2/1995 |
| WO | WO-95/21258 A1 | 8/1995 |
| WO | WO-95/31483 A1 | 11/1995 |
| WO | WO-96/04388 A1 | 2/1996 |
| WO | WO-96/08570 A1 | 3/1996 |
| WO | WO-96/18412 A1 | 6/1996 |
| WO | WO-96/40792 A1 | 12/1996 |
| WO | WO-97/00317 A1 | 1/1997 |
| WO | WO-97/00319 A2 | 1/1997 |
| WO | WO-97/24137 A1 | 7/1997 |
| WO | WO-97/24440 A1 | 7/1997 |
| WO | WO-97/30089 A1 | 8/1997 |
| WO | WO-97/33617 A1 | 9/1997 |
| WO | WO-97/33619 A1 | 9/1997 |
| WO | WO-97/34631 A1 | 9/1997 |
| WO | WO-97/43316 A1 | 11/1997 |
| WO | WO-98/00127 A1 | 1/1998 |
| WO | WO-98/28427 A1 | 7/1998 |
| WO | WO-98/30706 A1 | 7/1998 |
| WO | WO-98/46257 A1 | 10/1998 |
| WO | WO-98/52976 A1 | 11/1998 |
| WO | WO-99/02709 A1 | 1/1999 |
| WO | WO-99/03887 A1 | 1/1999 |
| WO | WO-99/29732 | 6/1999 |
| WO | WO-99/43713 | 9/1999 |
| WO | WO-99/52562 | 10/1999 |
| WO | WO-99/53958 A2 | 10/1999 |
| WO | WO-00/23472 A2 | 4/2000 |
| WO | WO-00/11033 | 5/2000 |
| WO | WO-00/34317 A2 | 6/2000 |
| WO | WO-00/40615 | 7/2000 |
| WO | WO-00/69913 | 11/2000 |
| WO | WO-01/03737 A1 | 1/2001 |
| WO | WO-01/07081 | 2/2001 |
| WO | WO-01/10912 A1 | 2/2001 |
| WO | WO-01/36489 A2 | 5/2001 |
| WO | WO-01/58957 | 8/2001 |
| WO | WO-02/02143 | 1/2002 |
| WO | WO-02/066514 A2 | 8/2002 |
| WO | WO-02/072605 | 9/2002 |

(56) References Cited

FOREIGN PATENT DOCUMENTS

| WO | WO-02/074783 A2 | 9/2002 |
|---|---|---|
| WO | WO-02/079232 | 10/2002 |
| WO | WO-02/079415 | 10/2002 |
| WO | WO-02/090566 | 11/2002 |
| WO | WO-03/015697 A2 | 2/2003 |
| WO | WO-03/048334 | 6/2003 |
| WO | WO-03/077834 A2 | 9/2003 |
| WO | WO-2006000448 A2 | 1/2006 |
| WO | WO-2006/074199 | 7/2006 |

OTHER PUBLICATIONS

Burgess, Shaheen, Ravera, Jaye, Donohue, and Winkles. Possible dissociation of the heparin binding and mitogenic activities of heparin binding (acidic fibroblast) growth factor-1 from its receptor binding activities by site directed mutagenesis of a single lysine residue. Journal of Cell Biology, 1990. vol. 111 pp. 2129-2138.*

Lazar, Watanabe, Dalton, and Sporn. Transforming growth factor alpha: mutation of aspartic acid 47 and leucine 48 results in different biological activities. Molecular and Cellular Biology, 1988. vol. 8 pp. 1247-1252.*

Firan, M., et al. (2001) "The MHC Class I-Related Receptor, FcRn, Plays an Essential Role in the Maternofetal Transfer of γ-Globin in Humans," International Immunology 13(8): 993-1002.

Kim, J., et al. (1994) "Catabolism of the Murine IgG1 Molecule: Evidence that Both CH2-CH3 Domain Interfaces are Required for Persistence of IgG1 in the Circulation of Mice," Scand. J. Immunol. 40: 457-465.

Martin, W., et al. (1999) "Characterization of the 2:1 Complex Between the Class I MHC-Related Fc Receptor and Its Fc Ligand in Solution," Biochemistry, 38: 12639-12647.

Roopenian, D., et al. (2007) "FcRn: The Neonatal Fc Receptor Comes of Age," Nat. Rev. Immunol 7(9): 715-725.

Shields, R., et al., (2001) "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, 276(9): 6591-6604.

Tesar, D., et al. (2006) "Ligand Valency Affects Transcytosis, Recycling and Intracellular Trafficking Mediated by the Neonatal Fc Receptor," Traffic, 7: 1127-1142.

Vidarsson, G., et al. (2006) "FcRn: An IgG Receptor on Phagocytes with a Novel Role in Phagocytosis," Blood, 108 (10): 3573-3579.

Ward, E., et al. (2003) "Evidence to Support the Cellular Mechanism Involved in Serum IgG Homeostasis in Humans," International Immunology 15(2): 187-195.

Angal "A single amino acid substitution abolishes the heterogeneity of chimeric mouse/human (IgG4) antibody" Mol Immunol. Jan. 1993;30(1):105-8.

Ghetie et al "Multiple roles for the major histocompatibility complex class I-related receptor FcRn" Annu Rev Immunol. 2000;18:739-66.

Gillies et al. "Improving the efficacy of antibody-interleukin 2 fusion proteins by reducing their interaction with Fc receptors" Cancer Res. May 1, 1999;59(9):2159-66.

Gurbaxani et al. "Analysis of a family of antibodies with different half-lives in mice fails to find a correlation between affinity for FcRn and serum half-life" Mol Immunol. Mar. 2006;43(9):1462-73. Epub Sep. 1, 2005.

International Search Report for PCT/EP2010/002377, mailed Augusut 4, 2010, 6 pages.

Written Opinion for PCT/EP2010/002377, mailed Aug. 4, 2010, 7 pages.

Davis et al. "Immunocytokines: amplification of anti-cancer immunity" Cancer Immunol Immunother. May 2003;52(5):297-308. Epub Jan. 31, 2003.

Lo et al. "High level expression and secretion of Fc-X fusion proteins in mammalian cells" Protein Eng. Jun. 1998;11(6):495-500.

Brusco et al. "Molecular characterization of immunoglobulin G4 gene isoallotypes" Eur J Immunogenet Oct. 1998;25(5):349-55.

Burmeister et al., "Crystal structure of the complex of rat neonatal Fc receptor with Fc" Nature Nov. 24, 1994;372(6504):379-83.

Kim et al. "Mapping the site on human IgG for binding of the MHC class I-related receptor, FcRn" Eur J Immunol Sep. 1999;29(9):2819-25.

Benacerraf et al. (1959) "The Clearance of Antigen Antibody Complexes from the Blood by the Reticulo-Endothelial System", J. Immunol., 82:131-7.

Beutler et al. (1988) "Tumor Necrosis, Cachexia, Shock, and Inflammation: A Common Mediator", Ann. Rev. Biochem., 57: 505-518.

Bitonti et al. "Pulmonary delivery of an erythropoietin Fc fusion protein in non-human primates through an immunoglobulin transport pathway" Proc Natl Acad Sci U S A. Jun. 29, 2004;101(26):9763-8. Epub Jun. 21, 2004.

Bitonti et al. "Transepithelial Absorption of an Erythropoietin-Fc Fusion Protein After Delivery to the Central Airways," Respiratory Drug Delivery, 8:309-312. (2002).

Bjorn et al. (2002) "Evaluation of Monoclonal Antibodies for the Development of Breast Cancer Immunotoxins" Cancer Research, 45:1214-1221.

Boulianne et al. (1984) "Production of Functional Chimaeric Mouse/Human Antibody," Nature, 312:643-6.

Bubenik et al. (1995) "Interleukin-2 Gene Therapy of Residual EL-4 Leukaemia Potentiates the Effect of Cyclophosphamide Pretreatment," J. Cancer Res. Clin. Oncol., 121:39-43.

Capon et al. (1989) "Designing CD4 immunoadhesins for AIDS therapy," Nature, 337:525-531.

Caton et al. (1986) "Structural and functional implications of a restricted antibody response to a defined antigenic region on the influenza virus hemagglutinin," The EMBO Journal, 5(7)1577-1587.

Chan et al. (1992) "Mechanisms of IFN-γ Induction by Natural Killer Cell Stimulatory Factor (NKSF/IL-12). Role of Transcription and mRNA Stability in the Synergistic Interaction Between NKSF and IL-2," J. Immunol., 148:92-98.

Chaudhary et al. (1988) "Selective killing of HIV-infected cells by recombinant human CD4-Pseudomonas exotoxin hybrid protein," Nature, vol. 335, pp. 370-372.

Chaudhary et al. (1989) "A recombinant immunotoxin consisting of two antibody variable domains fused to Pseudomonas exotoxin" Nature, vol. 339, pp. 394-397.

Cheon et al. (1994) "High-affinity binding sites for related fibroblast growth factor ligands reside within different receptor immunoglobulin-like domains," Proc. Natl. Acad. Sci. USA 91:989-993.

Cohen et al. (1998) "An Artificial Cell-Cycle Inhibitor Isolated From a Combinatorial Library" Proc Natl Acad Sci U S A. 95(24):14272-7.

Cohen. et al. (1996) "Human leptin characterization," Nature, 382:589.

Cole et al. (1997) "Human IgG2 Variants of Chimeric Anti-CD3 Are Nonmitogenic to T Cells," Journal of Immunology, 159:3613-3621.

Conner et al. (2004) "Ex vivo Evaluation of Anti-EpCAM Immunocytokine huKS-IL2 in Ovarian Cancer," J. Immunotherapy, 27:211-219.

Cruse et al. (1995) Illustrated Dictionary of Immunology, CRC Press, NY, p. 156-7.

Day et al. (1992) "Engineered disulfide bond greatly increases specific activity of recombinant murine interferon-beta," J Interferon Res. 12(2):139-43.

Dolman et al. (1998) "Suppression of Human Prostate Carcinoma Metastases in Severe Combined Immunodeficient Mice by Interleukin 2 Immunocytokine Therapy," Clin Cancer Res., 4(10):2551-7.

Fell et al. (1991) "Genetic Construction and Characterization of Fusion Protein Consisting of a Chimeric F(ab') with Specificity for Carcinomas and Human IL-2," The J. of Immunology, vol. 146, pp. 2446-2452.

Fell et al. (1992) "Chimeric L6 antitumor antibody," J. of Biol. Chem., 267(22):15552-15558.

Frost et al. (1997) "A Phase I/IB Trial of Murine Monoclonal Anti GD2 Antibody 14.G2a Plus Interleukin-2 in Children with Refractory Neuroblastoma," Cancer, 80:317-33.

(56) References Cited

OTHER PUBLICATIONS

Gan et al. (1999) "Specific enzyme-linked Immunosorbent Assays for Quantitation of Antibody-cytokine Fusion Proteins," *Clin. Diagn. Lab. Immunol.*, 6(2):236-42.

Gasson et al. (1984) "Purified Human Granulocyte Macrophage Colony-Stimulating Factor: Direct Action in Neutrophils", *Science*, 226:1339-134.

Gillies et al. (1990) "Antigen binding and biological activities of engineered mutant chimeric antibodies with human tumor specificities," *Hum. Antibod. Hybridomas* 1(1):47-54.

Gillies et al. (1989) "Expression of Human Anti-Tetanus toxoid antibody in Transfected Murine Myeloma Cells," *Bio/Technology*, 7:799-804.

Gillies et al. (1989) "High-Level Expression of Chimeric Antibodies Using Adapted cDNA Variable Region Cassettes," *J. Immunol. Methods*, 125:191-202.

Gillies et al. (1991) "Expression of Genetically Engineered Immunoconjugates of Lymphotoxin and a Chimeric Anti-ganglioside GD2 Antibody," *Hybridoma.*, 10(3):347-56.

Gillies et al. (1991) "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Gillies et al. (1992) "Antibody-Targeted Interleukin 2 Stimulates T-Cell Killing of Autologous Tumor Cells," *Proc. Natl. Acad. Science*, 89:1428-1432.

Gillies et al. (1993) "Biological Activity and In Vivo Clearance of Antitumor Antibody/Cytokine Fusion Proteins," *Bioconjugate Chem.*, 4: 230-235.

Gillies et al. (2002) "Bi-functional Cytokine Fusion Proteins for Gene Therapy and Antibody-targeted Treatment of Cancer," *Cancer Immunol. Immunother.*, 51(8):449-60.

Gillies et al. (2002) "Improved Circulating Half-life and Efficacy of an Antibody-interleukin 2 Immunocytokine Based on Reduced Intracellular Proteolysis," *Clin. Cancer Res.*, 8(1):210-6.

Gillies, et al. (1998) "Antibody-IL-12 fusion proteins are effective in SCID mouse models of prostate and colon carcinoma metastases," *Journal Immunology*, 160(12): 6195-6203.

Goeddel et al. (1986) "Tumor Necrosis Factors; Gene Structure and Biological Activities," *Pharm. Sciences*, pp. 597-609.

Gren et al. (1983) "A New Type of Leukocytic Interferon," *Dokl. Biochem.*, 269:91-95.

Grimaldi et al. (1989) "The t(5;14) Chromosomal Translocation in a Case of Acute Lymphocytic Leukemia Joins the Interleukin-3 Gene to the Immunoglobulin Heavy Chain Gene," *Blood*, 73(8): 2081-2085.

Gurewich et al. (1988) "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Guyre et al. (1997) "Increased potency of Fc-receptor-targeted antigens," *Cancer Immunol. Immunother.* 45:146-148.

Halin et al. (2002) "Enhancement of the antitumor activity of interleukin-12 by targeted delivery to neovasculature" *Nat Biotechnol.* 20(3):264-9.

Hank et al. (1996) "Activation of Human Effector Cells by a Tumor Reactive Recombinant Anti-ganglioside GD2 Interleukin-2 Fusion Protein (ch14.8-IL2)," *Clin Cancer Res.*, 2(12):1951-9.

Hank et al. (2003) "Determination of peak serum levels and immune response to the humanized anti-ganglioside antibody-interleukin-2 immunocytokine," *Methods Mol. Med.*, 85:123-31.

Harris et al. (1993) "Therapeutic Antibodies—the Coming of Age" *Tibtech*, 11:42-44.

Harris, (1995) "Processing of C-terminal lysine and arginine residues of proteins isolated from mammalian cell culture," *J. Chromatogr. A.*, 705:129-134.

Harvill et al. (1996) "In vivo properties of an IgG3-IL-2 fusion protein: A general strategy for immune potentiation." *Journal of Immunology*, 157(7): 3165-3170.

Harvill et al. (1995) "A IgG3-IL2 Fusion Protein Activates Complement, Binds FcYRI, Generates LAK Activity and Shows Enhanced Binding to the High Affinity IL-2R," *Immunotech.*, 1:95-105.

He et al. (1998) "Humanization and Pharmacokinetics of Monoclonal Antibody with Specificity for Both E- and P-Selectin," *J. Immunol.* 1029-1035.

Henkart, (1985) "Mechanism of Lymphocyte-Mediated Cytotoxicity," *Ann. Rev. Immunol.*, 3:31-58.

Herrmann et al. (1989) "Hematopoeitic Responses With Advanced Malignancy Treated With Recombinant Human Granulocyte-Macrophage Colony-Stimulating Factor," *Journal of Clinical Oncology*, 7(2):159-167.

Hezareh et al. (2001) "Effector Function Activities of a Panel of Mutants of a Broadly Neutralizing Antibody against Human Immunodeficiency Virus Type 1," *J. Virol.*, 75(24):12161-8.

Holden, et al. (2001) "Augmentation of Anti-Tumor Activity of KS-IL2 Immunocytokine with Chemotherapeutic Agents." *Proceedings of the American Association for Cancer Research*, 42: 683.

Holden, et al. (2001) "Augmentation of Antitumor activity of an Antibody-Interleukin 2 Immunocytokine with Chemotherapeutic Agents" *Clinical Cancer Research*, 7( 9):2862-2869.

Hoogenboom et al. (1991) "Construction and expression of antibody-tumor necrosis factor fusion proteins," *Molecular Immunology*, 28(9):1027-1037.

Hoogenboom et al. (1991) "Targeting of Tumor Necrosis Factor to Tumor Cells Secretion by Myeloma Cells of a Genetically Engineered Antibody-Tumor Necrosis Factor Hybrid Molecule," *Biochim. and Biophys. Acta*, 1096(4):345-354.

Hornick et al. (1999) "Pretreatment with a monoclonal antibody/interleukin-2 fusion protein directed against DNA enhances the delivery of therapeutic molecules to solid tumors" *Clin Cancer Res.* 5(1):51-60.

Hurn et al. (1980) "Production of Reagent Antibodies," *Methods in Enzymology*, 70: 104-142.

Imboden et al. (2001) "The Level of MHC Class I Expression of Murine Adenocarcinoma Can Change the Antitumor Effector Mechanism of Immunocytokine Therapy," *Cancer Res.*, 61(4):1500-7.

International Search Report for International Application No. PCT/EP2005/006925, mailed Dec. 19, 2005.

Jones et al. (2004) "The development of a modified human IFN-alpha2b linked to the Fc portion of human IgG1 as a novel potential therapeutic for the treatment of hepatitis C virus infection" *J Interferon Cytokine Res.* 24(9):560-72.

Zheng, et al. (1995) "Administration of noncytolytic IL-10/Fc in murine models of lipopolysaccaride-induced septic shock and allogenic islet transplantation," *Journal Immunology*, 154(10):5590-5600.

Jung et al. (1986) "Activation of human peripheral blood mononuclear cells by anti-T3: Killing of tumor target cells coated with anti-target-anti-T3 conjugates," *Proc. Natl. Acad. Sci. USA*, 83:4479-4483.

Kappel, et al. (1992) "Regulating gene expression in transgenic animals," *Current Opinion in Biotechnology* 3:548-553.

Karpovsky et al. (1984) "Production of Target-Specific Effector Cells using Hetero-Cross Linked Aggregate Containing Anti-Target Cell and AntiFcλ Receptor Antibodies," *Journal of Experimental Medicine*, 160(6):1686-1701.

Karpusas et al. (1997) "The crystal structure of human interferon beta at 2.2-A resolution" *Proc Natl Acad Sci U S A*. 94(22):11813-8.

Kendra et al. (1999) "Pharmacokinetics and stability of the ch 14.18-interleukin-2 fusion protein in mice," *Cancer Immunol. Immunotherapy*, 48:219-229.

Kim, et al. (1999) "Cytokine Molecular Adjuvants Modulate Immune Responses Induced by DNA Vaccine Constructs for HIV-1 and SIV" *Journal of Interferon and Cytokine Research*, 19:77-84.

King et al. (2004) "Phase I clinical trial of the immunocytokine EMD 273063 in melanoma patients" *J Clin Oncol.* 15;22(22):4463-73. Epub Oct. 13, 2004.

Ko et al. (2004) "Safety, Pharmcokinetics, and Biological Pharmacodynamics of the Immunocytokine EMD 273066 (huKS-IL2)," *J. Immunotherapy*, 27:232-239.

(56) References Cited

OTHER PUBLICATIONS

Kranz et al. (1984) "Attachment of an anti-receptor antibody to non-target cells renders them susceptible to lysis by a clone of cytotoxic T lymphocytes", *Proc. Natl. Acad. Sci. USA*, 81:7922-7926.

Kushner et al. (2001) "Phase II Trial of the Anti-GD2 Monoclonal-macrophage-colony-stimulating Factor for Neuroblastoma," *J. Clin. Oncol.*, 19:4189-94.

Lawn et al. (1981) "DNA sequence of a major human leukocyte interferon gene" *Proc Natl Acad Sci U S A*. 78(9):5435-9.

LeBerthon et al. (1991) "Enhanced Tumor Uptake of Macromolecules Induced by a Novel Vasoactive Interleukin 2 Immunoconjugate," *Cancer Research*, 51:2694-2698.

Linsley et al. (1991) "CTLA-4 is a Second Receptor for B Cell Activation Antigen B7," *Journal of Experimental Medicine*, 174(3):561-569.

Liu et al. (1985) "Heteroantibody Duplexes Target Cells for Lysis by Cytotoxic T Lymphocytes", *Proc. Natl. Acad. Sci. USA*, 82:8648-8652.

Liu et al. (1988) "Hormone Conjugated with Antibody to CD3 Mediates Cytotoxic T Cell Lysis of Human Melanoma Cells," *Science*, 239: 395-398.

Lo et al. (2005) "Engineering a pharmacologically superior form of leptin for the treatment of obesity," *Protein Eng Des Sel*. 18(1):1-10.

Lo et al. (1992) "Expression and Secretion of an Assembled Tetrameric CH2-deleted Antibody in *E. coli.*," *Hum. Antibod. Hybridomas*, 3:123-128.

Lode et al. (1997) "Targeted Interleukin-2 Therapy for Spontaneous Neuroblastoma Metastases to Bone Marrow," *J. Natl. Cancer Inst.*, 89(21):1586-94.

Lode et al. (1998),"Immunocytokines: a promising approach to cancer immunotherapy," *Pharmcol. Thera.*, 80:277-292.

Lode et al. (1998) "Natural Killer Cell-Mediated Eradication of Neuroblastoma Metastases to Bone Marrow by Targeted Interleukin-2 Therapy," *Blood*, 91(5):1706-1715.

Lode et al. (1999) "Synergy between an antiangiogenic integrin $\alpha_v$ antagonist and an antibody-cytokine fusion protein eradicates spontaneous tumor metastases," *Proc. Natl. Acad. Sci. USA*, 96:1591-1596.

Lode et al. (1999) "Tumor-targeted IL-2 amplifies T cell-mediated immune response induced by gene therapy with single-chain IL-12," *Proc. Natl. Acad. Sci. USA*, 96:8591-8596.

Lode et al. (2000) "Amplification of T Cell Mediated Immune Responses by Antibody-Cytokine Fusion Proteins," *Immunological Investigations*, 29(2):117-120.

Lode et al. (2000) "Melanoma immunotherapy by targeted Il-2 depends on CD4(+) T-cell help mediated by CD40/CD40L interaction," *J. Clin. Invest.*, 105(11):1623-30.

Lode et al. (2000) "What to do with targeted IL-2," *Drugs Today*, 36(5):321-36.

MacLean et al. (1996) "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Mark et al. (1992) "Expression and characterization of hepatocyte growth factor receptor-IgG fusion proteins." *Journal of Biological Chemistry*, 267(36):26166-26171.

Martin et al. (2001) "Crystal structure at 2.8 A of an FcRn/heterodimeric Fc complex: mechanism of pH-dependent binding," *Mol Cell*. 7(4):867-77.

McMahan et al. (1991) "A Novel IL-1 Receptor, Cloned From B-Cells by Mammalian Expression is Expressed in Many Cell Types," *EMBO J.*, 10:2821-32.

Medesan et al. (1997) "Delineation of the Amino Acid Residues Involved in Transcytosis and Catabolism of Mouse IgG1[1]," *Journal Immunology*, 158(5): 2211-2217.

Metelitsa et al. (2002) "Antidisialoganglioside/granulocyte Macrophage-colony-stimulating Factor Fusion Protein Facilitates Neutrophil Antibody-dependent Cellular Cytotoxicity and Depends on FcγRII (CD32) and Mac-1 (CD11b/CD18) for Enhanced Effector Cell Adhesion and Azurophil Granule Exocytosis," *Blood*, 99(11):4166-73.

Mickle et al. (2000) "Genotype-phenotype relationships in cystic fibrosis" *Med Clin North Am*. 84(3):597-607.

Miyake et al. (1988) "Synthesis of Recombinant Human Single-Chain Urokinase-Type Plasminogen Activator Variants Resistant to Plasmin and Thrombin," *J. Biochem.*, 104:643-647.

Morrison et al. (1984) "Chimeric human antibody molecules: mouse antigen-binding domains with human constant region domains" *Proc Natl Acad Sci U S A*. 81(21):6851-5.

Mueller et al. (1997) "Humanized Porcine VCAM-specific Monoclonal Antibodies with Chimeric IgG2/G4 Constant Regions Block Human Leukocyte Binding to Porcine Endothelial Cells," *Molecular Immunology*, 34(6):441-452.

Mueller et al. (1990) "Enhancement of Antibody-Dependent Cytotoxicity With a Chimeric Anti-GD2 Antibody," *J. Immunology*, 144(4):1382-1386.

Mueller et al. (1990) "Serum Half-Life and Tumor Localization of a Chimeric Antibody Deleted of the CH2 Domain and Directed Against the Disialoganglioside GD2," *Proc. Natl. Acad. Sci. USA.*, 87:5702-5705.

Murphy et al. (1986) "Genetic construction, expression, and melanoma-selective cytotoxicity of a diptheria toxin-related α-melanocyte-stimulating hormone fusion protein," *Proc. Natl. Acad. Sci. USA*, 83:8258-8262.

Murphy (1988) "Diphtheria-related peptide hormone gene fusions: A molecular gene approach t chimeric toxin development," *Immunotoxins*, pp. 123-140.

Naramura et al. (1994) "Mechanisms of Cellular Cytotoxicity Mediated by a Recombinant Antibody-IL2 Fusion Protein against Human Melanoma Cells," *Immunology Letters*, 39(1):91-9.

Naramura et al. (1993) "Therapeutic Potential of Chimeric and Murine Anti-(Epidermal Growth Factor Receptor) Antibodies in a Metastasis Model for Human Melanoma," *Cancer Immuno. Immunother.*, 37:343-349.

Nastala et al. (1994) "Recombinant IL-12 Administration Induces Tumor Regression in Association with IFN-γ Production," *J. Immunol.*, 153:1697-706.

Neal et al. (2004) "Enhanced activity of hu14.18-IL2 immunocytokine against murine NXS2 neuroblastoma when combined with interleukin 2 therapy" *Clin Cancer Res*. 10(14):4839-47.

Neal et al. (2003) "NXS2 Murine Neuroblastomas Express Increased Levels of MHC Class I Antigens upon Recurrence Following NK-dependent Immunotherapy," *Cancer Immunol Immunother.*, 53:41-52.

Nedwin et al. (1985) "Human Lymphotoxin and Tumor Necrosis Factor Genes: Structure, Homology and Chromosomal Localization," *Nucleic Acids Research*, 13(17):6363-6373.

Nelles et al. (1987) "Characterization of Recombinant Human Single Chain Urokinase-Type Plasminogen Activator Mutants Produced by Site-Specific Mutagenesis of Lysine 158," *J. Biol. Chem.*, 262(12):5682-5689.

Neuberger, et al. (1984) "Recombinant Antibodies Possessing Novel Effector Functions.," *Nature*, 312: 604-608.

Ngo et al. (1994) "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.

Niethammer et al. (2001) "Targeted interleukin 2 therapy enhances protective immunity induced by an autologous oral DNA vaccine against murine melanoma" *Cancer Res*. 61(16):6178-84.

Zhu et al. (2001) "MHC class I-related neonatal Fc receptor for IgG is functionally expressed in monocytes, intestinal macrophages, and dendritic cells" *J Immunol*. 166(5):3266-76.

Pancook et al. (1996) "Eradication of Established Hepatic Human Neuroblastoma Metastases in Mice with Severe Combined Immunodeficiency by Antibody-targeted Interleukin-2," *Cancer Immunol. Immunother.*, 42(2):88-92.

Pedley et al. (1999) "Enhancement of antibody-directed enzyme prodrug therapy in colorectal xenografts by an antivascular agent" *Cancer Res*. 59(16):3998-4003.

(56) References Cited

OTHER PUBLICATIONS

Perez et al. (1986) "Specific Targeting of Human Peripheral Blood T Cells by Heteroaggregates Containing Anti-T3 Crosslinked to Anti-Target Cell Antibodies," *J. Exp. Medicine*, 163:166-178.
Poon et al. (1995) "Structure and function of several anti-dansyl chimeric antibodies formed by domain interchanges between human IgM and mouse IgG2b" *J Biol Chem.* 270(15):8571-7.
Radhakrishnan et al. (1996) "Zinc mediated dimer of human interferon-alpha 2b revealed by X-ray crystallography" *Structure.* 4(12):1453-63.
Reisfeld et al. (1996) "Antibody-interleukin 2 fusion proteins: a new approach to cancer therapy," *J Clin Lab Anal.*, 10(3):160-6.
Reisfeld et al. (1996) "Involvement of B Lymphocytes in the Growth Inhibition of Human Pulmonary Melanoma Metastases in Athymic nu/nu Mice by an Antibody-lymphotoxin Fusion Protein," *Cancer Res.*, 56(8):1707-12.
Reisfeld et al. (1996) "Recombinant antibody fusion proteins for cancer immunotherapy," *Current Topics in Microbiology and Immunology*, pp. 27-53.
Reisfeld et al. (1997) "Immunocytokines: a new approach to immunotherapy of melanoma," *Melanoma Research*, vol. 7. Suppl. 2, pp. S99-S106.
Rosenberg, (1988) "Immunotherapy of Cancer Using Interleukin 2: current status and future prospects," *Immunology Today*, 9(2):58-62.
Ruehlmann et al. (2001) "MIG (CIXCL9) Chemokine Gene Therapy Combines with Antibody-cytokine Fusion Protein to Suppress Growth and Dissemination of Murine Colon Carcinoma," *Cancer Res.*, 61(23):8498-503.
Runkel et al. (1998) "Structural and functional differences between glycosylated and non-glycosylated forms of human interferon-beta (IFN-beta)" *Pharm Res.* 15(4):641-9.
Runkel et al. (2000) "Systematic mutational mapping of sites on human interferon-beta-1a that are important for receptor binding and functional activity" *Biochemistry.* 39(10):2538-51.
Sabzevari et al. (1994) "A Recombinant Antibody-interleukin 2 Fusion Protein Suppresses Growth of Hepatic Human Severe Combined Immunodeficiency Mice," *Proc. Natl. Acad. Sci. USA*, 91(20):9626-30.
Sakano et al. (1980) "Two types of somatic recombination are necessary for the generation of complete immunoglobulin heavy-chain genes" *Nature.* 286(5774):676-83.
Schnee et al. (1987) "Construction and expression of a recombinant antibody-targeted plasminogen activator," *Proc. Natl. Acad. Sci. USA*, 84:6904-6908.
Senior et al. (2000) "Cleavage of a recombinant human immunoglobulin A2 (IgA2)-IgA1 hybrid antibody by certain bacterial IgA1 proteases" *Infect Immun.* 68(2):463-9.
Senter et al. (1988) "Anti-tumor effects of antibody-alkaline phosphatase conjugates in combination with etoposide phosphate," *Proc. Natl. Acad. Sci USA*, 85(13)4842-4846.
Shin et al. (1990) "Expression and characterization of an antibody binding specificity joined to insulin-like growth factor 1: potential applications for cellular targeting" *Proc Natl Acad Sci U S A.* 87(14):5322-6.
Shinkawa et al. (2003) "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol.Chem.*, 278:3466-3473.
Spiekermann et al. (2002) "Receptor-mediated Immunoglobulin G Transport Across Mucosal Barriers in Adult Life: Functional Expression of FcRn in the Mammalian Lung," *J. Exp. Med.*, 196:303-310.
Stevenson et al. (1997) "Conjugation of Human Fcγ in Closed-Hinge or Open-Hinge Configuration to Fab'γ and Analogous Ligands," *Journal of Immunology*, 158:2242-2250.
Stewart et al (1987) "Chemical mutagenesis of human interferon-beta: construction, expression in *E. coli*, and biological activity of sodium bisulfite-induced mutations" *DNA.* 6(2):119-28.
Stickler et al. (2004) "The HLA-DR2 haplotype is associated with an increased proliferative response to the immunodominant CD4(+) T-cell epitope in human interferon-beta" *Genes Immun.* 5(1):1-7.
Takai (2002) "Roles of Fc receptors in autoimmunity" *Nat Rev Immunol.* 2(8):580-92.
Taniguchi et al. (1980) "Expression of the human fibroblast interferon gene in *Escherichia coli*" *Proc Natl Acad Sci U S A.* 77(9):5230-3.
Zuckier et al. (1998) "Chimeric human-mouse IgG antibodies with shuffled constant region exons demonstrate that multiple domains contribute to in vivo half-life" *Cancer Res.* 58(17):3905-8.
Tao et al. (1989) "Studies of Aglycosylated Chimeric Mouse IgG: Role of Carbohydrate in the Structure and Effector Functions Mediated by the Human IgG Constant Region," *Journal of Immunology*, 143(8):2595-2601.
Tao et al. (1993) "Structural Features of Human Immunoglobulin G that Determine Isotype-Differences in Complement Activation," *Journal of Experimental Medicine*, 178(2):661-667.
Thommesen et al. (2000) "Lysine 322 in the Human IgG3 CH2 Domain is Crucial for Antibody Dependent Complement Activation," *Mol. Immunol.*, 37(16):995-1004.
Till et al. (1988) "An Assay that Predicts the Ability of Monoclonal Antibodies to Form Potent Ricin A Chain-containing Immunotoxins," *Cancer Research*, 48(5):119-1123.
Till et al. (1988) "HIV-Infected Cells are Killed by rCD4-Ricin A Chain," *Science*, 242:1166-1168.
Verhoeyen et al. (1988) "Reshaping Human Antibodies: Grafting an Antilysozyme Activity," *Science* 239:1534-1536.
Ward et al. (1995) "The effector functions of immunoglobulins: implications for therapy" *Ther Immunol.* 2(2):77-94.
Williams et al. (1986) "Production of antibody-tagged enzymes by myeloma cells: application to DNA polymerase 1 Klenow fragment," *Gene*, 43:319-324.
Woof et al. (1986) "Localisation of the monocyte-binding region on human immunoglobulin G" *Mol Immunol.* 23(3):319-30.
Wooley et al. (1993) "Influence of a Recombinant Human Soluble Tumor Necrosis Factor Receptor FC Fusion Protein on Type II Collagen-Induced Arthritis in Mice," *J. Immunol.* 151: 6602-6607.
Written Opinion of the International Searching Authority for International Application No. PCT/EP2005/006925, mailed Dec. 19, 2005 (5 pages).
Xiang et al. (1997) "Elimination of Established Murine Colon Carcinoma Metastases by Antibody-Interleukin 2 Fusion Protein Therapy," *Cancer Research*, 57:4948-4955.
Xu et al. (1994) "Residue at Position 331 in the IgG1 and IgG4 CH2 Domains Contributes to Their Differential Ability to Bind and Activate Complement," *J. Biol. Chem.*, 269(5):3469-3474.

\* cited by examiner

A.  B.  C.

D.  E.  F.

A.   B.   C.

D.   E.   F.

A.

B.

C..

D..

```
                              SEQUENCE LISTING

<160> NUMBER OF SEQ ID NOS: 14

<210> SEQ ID NO 1
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Ile Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 2
<211> LENGTH: 181
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 2

Gly Gly Gly Gly Ser Gly Gly Gly Ser Gly Gly Gly Ser Gly Met
1               5                   10                  15

Ser Tyr Asn Leu Leu Gly Phe Leu Gln Arg Ser Ser Asn Phe Gln Ser
                20                  25                  30

Gln Lys Leu Leu Trp Gln Leu Asn Gly Arg Leu Glu Tyr Cys Leu Lys
            35                  40                  45

Asp Arg Met Asn Phe Asp Ile Pro Glu Glu Ile Lys Gln Leu Gln Gln
50                  55                  60

Phe Gln Lys Glu Asp Ala Ala Thr Ile Tyr Glu Met Leu Gln Asn
65              70                  75                  80

Ile Phe Ala Ile Phe Arg Gln Asp Ser Ser Ser Thr Gly Trp Asn Glu
                85                  90                  95

Thr Ile Val Glu Asn Leu Leu Ala Asn Val Tyr His Gln Ile Asn His
            100                 105                 110

Leu Lys Thr Val Leu Glu Glu Lys Leu Glu Lys Glu Asp Phe Thr Arg
        115                 120                 125

Gly Lys Leu Met Ser Ser Leu His Leu Lys Arg Tyr Tyr Gly Arg Ile
130                 135                 140

Leu Ala Tyr Leu Lys Ala Lys Glu Tyr Ser Ala Cys Ala Trp Thr Ile
145                 150                 155                 160

Val Arg Val Glu Ile Leu Arg Asn Phe Tyr Phe Ile Asn Arg Leu Thr
                165                 170                 175

Gly Tyr Leu Arg Asn
            180

<210> SEQ ID NO 3
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Glu Leu Pro Val Arg Leu Leu Val Leu Met Phe Trp Ile Pro Ala
1               5                   10                  15

Ser Leu Ser Glu Pro Lys Ser Ser Asp Lys Thr His Thr Cys Pro Pro
                20                  25                  30

Cys Pro Ala Pro Glu Phe Leu Gly Gly Pro Ser Val Phe Leu Phe Pro
            35                  40                  45

Pro Lys Pro Lys Asp Thr Leu Met Ile Ser Arg Thr Pro Glu Val Thr
        50                  55                  60

Cys Val Val Val Asp Val Ser Gln Glu Asp Pro Glu Val Gln Phe Asn
65                  70                  75                  80

Trp Tyr Val Asp Gly Val Glu Val His Asn Ala Lys Thr Lys Pro Arg
                85                  90                  95

Glu Glu Gln Phe Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Gly Leu Pro Ser Ser Ile Glu Lys Thr Ile Ser Lys Ala Lys
130                 135                 140
```

Gly Gln Pro Arg Glu Pro Gln Val Tyr Thr Leu Pro Pro Ser Gln Glu
145                 150                 155                 160

Glu Met Thr Lys Asn Gln Val Ser Leu Thr Cys Leu Val Lys Gly Phe
            165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
        210                 215                 220

Asn Ile Phe Ser Cys Ser Val Met His Glu Ala Leu His Asn His Tyr
225                 230                 235                 240

Thr Gln Lys Ser Leu Ser Leu Ser Pro Gly Lys
            245                 250

<210> SEQ ID NO 4
<211> LENGTH: 1352
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atggagttgc ctgttaggct gttggtgctg atgttctgga ttcctggtga ggagagaggg      60
aagtgaggga ggagaatgga cagggagcag gagcactgaa tcccattgct cattccatgt     120
attctggcat gggtgagaag atgggtctta tcctccagca tggggcctct ggggtgaata     180
cttgttagag ggaggttcca gatgggaaca tgtgctataa tgaagattat gaaatggatg     240
cctgggatgg tctaagtaat gcctagaagt gactagacac ttgcaattca ctttttttgg     300
taagaagaga tttttaggct ataaaaaaat gttatgtaaa aataaacatc acagttgaaa     360
taaaaaaaaa tataaggatg ttcatgaatt ttgtgtataa ctatgtattt ctctctcatt     420
gtttcagctt ccttaagcga gcccaaatct tctgacaaaa ctcacacatg cccaccgtgc     480
ccaggtaagc cagcccaggc ctcgccctcc agctcaaggc gggacaggtg ccctagagta     540
gcctgcatcc agggacaggc cccagccggg tgctgacgca tccacctcca tctcttcctc     600
agcacctgag ttcctggggg gaccatcagt cttcctgttc cccccaaaac ccaaggacac     660
tctcatgatc tcccggaccc ctgaggtcac gtgcgtggtg gtggacgtga gccaggaaga     720
ccccgaggtc cagttcaact ggtacgtgga tggcgtggag gtgcataatg ccaagacaaa     780
gccgcgggag gagcagttca acagcacgta ccgtgtggtc agcgtcctca ccgtcctgca     840
ccaggactgg ctgaacggca aggagtacaa gtgcaaggtc tccaacaaag gcctcccgtc     900
ctccatcgag aaaaccatct ccaaagccaa aggtgggacc cacggggtgc gagggccaca     960
tggacagagg tcagctcggc ccaccctctg ccctgggagt gaccgctgtg ccaacctctg    1020
tccctacagg gcagccccga gagccacagg tgtacaccct gcccccatcc caggaggaga    1080
tgaccaagaa ccaggtcagc ctgacctgcc tggtcaaagg cttctacccc agcgacatcg    1140
ccgtggagtg ggagagcaat gggcagccgg agaacaacta caagaccacg cctcccgtgc    1200
tggactccga cggctccttc ttcctctaca gcaagctcac cgtggacaag agcaggtggc    1260 agcagggaa catcttctca tgctccgtga tgcatgaggc tctgcacaac cactacacgc    1320
agaagagcct ctccctgtcc ccgggtaaat ga                                  1352

```
<210> SEQ ID NO 5
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Glu Leu Pro Val Arg Leu Leu Val Leu Met Phe Trp Ile Pro Ala
1               5                   10                  15

Ser Leu Ser Glu Pro Lys Ser Ser Asp Lys Thr His Thr Cys Pro Pro
            20                  25                  30

Cys Pro Ala Pro Glu Phe Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser Gln Glu Asp Pro Glu Val Gln Phe Asn
65                  70                  75                  80

Trp Tyr Val Asp Gly Val Glu Val His Asn Ala Lys Thr Lys Pro Arg
                85                  90                  95

Glu Glu Gln Phe Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Gly Leu Pro Ser Ser Ile Glu Lys Thr Ile Ser Lys Ala Lys
    130                 135                 140

Gly Gln Pro Arg Glu Pro Gln Val Tyr Thr Leu Pro Pro Ser Gln Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Ile Phe Ser Cys Ser Val Met His Glu Ala Leu His Asn His Tyr
225                 230                 235                 240

Thr Gln Lys Ser Leu Ser Leu Ser Pro Gly Ala Gly Gly Gly Gly Ser
                245                 250                 255

Gly Gly Gly Gly Ser Gly Gly Ser Gly Met Ser Tyr Asn Leu Leu
            260                 265                 270

Gly Phe Leu Gln Arg Ser Ser Asn Phe Gln Ser Gln Lys Leu Leu Trp
        275                 280                 285

Gln Leu Asn Gly Arg Leu Glu Tyr Cys Leu Lys Asp Arg Met Asn Phe
    290                 295                 300

Asp Ile Pro Glu Glu Ile Lys Gln Leu Gln Gln Phe Gln Lys Glu Asp
305                 310                 315                 320

Ala Ala Ala Thr Ile Tyr Glu Met Leu Gln Asn Ile Phe Ala Ile Phe
                325                 330                 335

Arg Gln Asp Ser Ser Ser Thr Gly Trp Asn Glu Thr Ile Val Glu Asn
            340                 345                 350

Leu Leu Ala Asn Val Tyr His Gln Ile Asn His Leu Lys Thr Val Leu
        355                 360                 365
```

```
Glu Glu Lys Leu Glu Lys Glu Asp Phe Thr Arg Gly Lys Leu Met Ser
    370                 375                 380

Ser Leu His Leu Lys Arg Tyr Tyr Gly Arg Ile Leu Ala Tyr Leu Lys
385                 390                 395                 400

Ala Lys Glu Tyr Ser Ala Cys Ala Trp Thr Ile Val Arg Val Glu Ile
                405                 410                 415

Leu Arg Asn Phe Tyr Phe Ile Asn Arg Leu Thr Gly Tyr Leu Arg Asn
                420                 425                 430

<210> SEQ ID NO 6
<211> LENGTH: 1895
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggagttgc ctgttaggct gttggtgctg atgttctgga ttcctggtga ggagagaggg      60
aagtgaggga ggagaatgga cagggagcag gagcactgaa tcccattgct cattccatgt     120
attctggcat gggtgagaag atgggtctta tcctccagca tggggcctct ggggtgaata     180
cttgttagag ggaggttcca gatgggaaca tgtgctataa tgaagattat gaaatggatg     240
cctgggatgg tctaagtaat gcctagaagt gactagacac ttgcaattca cttttttgg     300 taagaagaga ttttaggct ataaaaaaat gttatgtaaa aataaacatc acagttgaaa     360 taaaaaaaa tataaggatg ttcatgaatt ttgtgtataa ctatgtattt ctctctcatt     420
gtttcagctt ccttaagcga gcccaaatct tctgacaaaa ctcacacatg cccaccgtgc     480
ccaggtaagc cagcccaggc ctcgccctcc agctcaaggc gggacaggtg cccctagagta     540 gcctgcatcc agggacaggc cccagccggg tgctgacgca tccacctcca tctcttcctc     600
agcacctgag ttcctggggg gaccatcagt cttcctgttc cccccaaaac ccaaggacac     660
tctcatgatc tcccggaccc ctgaggtcac gtgcgtggtg gtggacgtga gccaggaaga     720
ccccgaggtc cagttcaact ggtacgtgga tggcgtggag gtgcataatg ccaagacaaa     780
gccgcgggag gagcagttca acagcacgta ccgtgtggtc agcgtcctca ccgtcctgca     840
ccaggactgg ctgaacggca aggagtacaa gtgcaaggtc tccaacaaag cctcccgtc      900 ctccatcgag aaaaccatct ccaaagccaa aggtgggacc cacggggtgc gagggccaca     960
tggacagagg tcagctcggc ccaccctctg ccctgggagt gaccgctgtg ccaacctctg    1020
tccctacagg gcagccccga gagccacagg tgtacaccct gcccccatcc caggaggaga    1080
tgaccaagaa ccaggtcagc ctgacctgcc tggtcaaagg cttctacccc agcgacatcg    1140
ccgtggagtg ggagagcaat gggcagccgg agaacaacta caagaccacg cctcccgtgc    1200
tggactccga cggctccttc ttcctctaca gcaagctcac cgtggacaag agcaggtggc    1260 agcagggaa catcttctca tgctccgtga tgcatgagge tctgcacaac cactacacgc    1320
agaagagcct ctccctgtcc ccgggtgcag gggcgggggg cagcggggg ggaggatccg    1380 gcggggctc gggtatgagc tacaacttgc ttgattcct acaaagaagc agcaattttc    1440
agagtcagaa gctcctgtgg caattgaatg ggaggcttga atattgcctc aaggacagga    1500
tgaactttga catccctgag gagattaagc agctgcagca gttccagaag gaggacgccg    1560
cagccaccat ctatgagatg ctccagaaca tctttgctat tttcagacaa gattcatcta    1620
gcactggctg gaatgagact attgttgaga acctcctggc taatgtctat catcagataa    1680
```

```
accatctgaa gacagtcctg gaagaaaaac tggagaaaga agatttcacc aggggaaaac    1740
tcatgagcag tctgcacctg aaaagatatt atgggaggat tctggcctac ctgaaggcca    1800
aggagtacag tgcctgtgcc tggaccatag tcagagtgga aatcctaagg aacttttact    1860
tcattaacag acttacaggt tacctccgaa actga                               1895
```

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Ser Lys Tyr Gly Pro Pro Cys Pro Ser Cys Pro
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Pro Lys Ser Ser Asp Lys Thr His Thr Cys Pro Pro Cys Pro
1               5                   10                  15

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
cttaagcgag tccaaatatg gtcccccatg cccatcatgc ccag                      44
```

<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
cttaagcgag cccaaatctt ctgacaaaac tcacacatgc ccaccgtgcc cag             53
```

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
tctagaccac catggag                                                    17
```

```
<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggctctgcac aacgcgtaca cgcagaagag                                          30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcttctgcg tgtacgcgtt gtgcagagcc                                          30

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly Ser Gly Gly Gly Gly Ser Gly Gly Gly Ser Gly
1               5                   10                  15
```

ANTIBODY FUSION PROTEINS WITH A MODIFIED FCRN BINDING SITE

REFERENCE TO RELATED APPLICATIONS

This application claims the benefit of and priority to U.S. Provisional Patent Application No. 61/171,650, filed Apr. 22, 2009, the complete disclosure of which is incorporated herein by reference.

BACKGROUND

An antibody fusion protein linking a protein of interest to an immunoglobulin constant region possesses both the biological activity of the linked protein as well as the advantages associated with the presence of the immunoglobulin moiety. The creation of such fusion proteins helps to ensure the efficient production and secretion of proteins of interest. Furthermore, these fusion proteins often exhibit novel properties such as increased circulating half-life that are of significant therapeutic advantage.

In adult mammals, FcRn, also known as the neonatal Fc receptor, plays a key role in maintaining serum antibody levels by acting as a protective receptor that binds and salvages antibodies of the IgG isotype from degradation. IgG molecules are endocytosed by endothelial cells, and if they bind to FcRn, are recycled out into circulation. In contrast, IgG molecules that do not bind to FcRn enter the cells and are targeted to the lysosomal pathway where they are degraded. A variant IgG1 in which His435 is mutated to alanine results in the selective loss of FcRn binding and a significantly reduced serum half-life (Firan et al. 2001, *International Immunology* 13:993).

The Fc portion of an IgG molecules includes two identical polypeptide chains, with each polypeptide chain engaging a single FcRn molecule through its FcRn binding site (Martin et al., 1999, *Biochemistry* 38:12639). Earlier studies indicate that each Fc portion requires both FcRn binding sites for serum persistence. A heterodimeric Fc fragment containing a wild-type FcRn-binding polypeptide chain and a mutated non-FcRn-binding polypeptide chain has a significantly reduced serum half-life compared to a homodimeric wild-type Fc fragment (Kim et al., 1994, *Scand. J. Immunol.* 40:457-465). Such a heterodimeric Fc fragment containing only one FcRn binding site is recycled less efficiently than a homodimeric wild-type Fc fragment and is preferentially trafficked to lysosomes for degradation (Tesar et al., 2006, *Traffic* 7:1127). These observations have direct relevance to the effective application of therapeutics involving FcRn binding partners including IgG antibodies or their Fc portions. For example, U.S. Pat. No. 7,348,004 describes a fusion protein that specifically requires intact FcRn binding or even enhanced FcRn binding for its improved biological properties such as increased serum half-life and enhanced bioavailability.

More recent studies have identified the expression of FcRn in phagocytes and suggested a novel role of FcRn in IgG-mediated phagocytosis (Vidarsson et al. 2006, *Blood* 108: 3573). IgG-opsonized pathogens are internalized into phagosomes by FcRn, providing an effective means to mark pathogens for ingestion and destruction by phagocytes. The IgG1 variant with a H435A mutation exhibits significantly reduced opsonization activity.

SUMMARY OF THE INVENTION

The present invention is based in part on the surprising discovery that an antibody fusion protein with a mutation in one of its constituent immunoglobulin constant region polypeptide chains that reduces or eliminates FcRn binding exhibits comparable biological properties such as prolonged circulating half-life as corresponding fusion proteins without the mutation. Furthermore, given the role of FcRn in IgG-mediated phagocytosis, it is contemplated that the antibody fusion protein with a mutation that reduces FcRn binding may have low opsonization activity leading to reduced immunogenicity.

The present invention provides methods and compositions for expressing soluble, biologically active antibody fusion proteins with a mutation in the FcRn binding site that reduces FcRn binding. The fusion protein includes two polypeptide chains. The first polypeptide chain includes a biologically active molecule linked to at least a portion of an immunoglobulin constant region, and the second polypeptide chain includes at least a portion of an immunoglobulin constant region. The amino acid sequence of the portion of the immunoglobulin constant region of one of the polypeptide chains differs from the amino acid sequence of the portion of the immunoglobulin constant region of the second polypeptide chain in that it contains a mutation in the FcRn binding site. The difference can be an amino acid deletion, insertion, substitution, or modification. In one embodiment, the difference is an amino acid substitution. In a further embodiment, the amino acid substitution is H435A.

The invention relates to fusion proteins linking a biologically active molecule to at least a portion of an immunoglobulin constant region. The biologically active molecule may be linked to the amino-terminus of the immunoglobulin constant region. Alternatively, the biologically active molecule may be linked to the carboxy-terminus of the immunoglobulin constant region. In a further embodiment, the fusion protein may include two biologically active molecules linked to two polypeptide chains of at least a portion of an immunoglobulin constant region.

The invention relates to fusion proteins that include at least a portion of the immunoglobulin constant region. It is contemplated that the portion of the immunoglobulin constant region can be an Fc fragment. In various embodiments, the Fc fragment is the Fc fragment of an IgG1, IgG2, IgG3, or IgG4. In another embodiment, the fusion protein includes an immunoglobulin variable region in at least one of the polypeptide chains.

The present invention contemplates the use of any biologically active molecule as the therapeutic molecule of the invention. For example, the biologically active molecule can be a human interferon, such as interferon-β. To improve folding and to reduce aggregation, an interferon-β sequence can include an amino acid alteration of at least one of positions 17, 50, 57, 130, 131, 136, and 140 corresponding to native, mature interferon-β. The alteration can be an amino acid substitution. In one embodiment, the amino acid substitution is selected from the group consisting of C17S, C17A, C17V, C17M, F50H, L57A, L130A, H131A, K136A, H140A, and H140T. In another embodiment, the biologically active molecule is a growth factor such as human erythropoietin. In yet another embodiment, the biologically active molecule is a hormone such as human growth hormone. Alternatively, the biologically active molecule can be a polypeptide, a small molecule, or a nucleic acid.

The invention also provides methods for encoding and expressing fusion proteins of the invention. For example, one aspect of the invention relates to a nucleic acid encoding a polypeptide chain that includes a biologically active molecule and at least a portion of an immunoglobulin constant region comprising a mutation that reduces FcRn binding. In another aspect, the invention relates to a composition of one nucleic acid encoding a polypeptide chain that includes a biologically active molecule and at least a portion of an immunoglobulin constant region, and a second nucleic acid encoding a second polypeptide chain that includes at least a portion of an immunoglobulin constant region. One of the nucleic acid sequences contains a mutation in the FcRn binding site. In one embodiment, the mutation is an amino acid substitution. In a further embodiment, the amino acid substitution is H435A. In another aspect, the nucleic acid molecule or the nucleic acid composition of the invention can be incorporated within a replicable expression vector, which can then be introduced into a host cell and be recombined with and integrated into the host cell genome. The replicable expression vector can include the aforementioned nucleic acid or the nucleic acid composition. In another embodiment, the invention encompasses the host cells containing the aforementioned nucleic acid or the nucleic acid composition.

The invention herein provides for a pharmaceutical composition comprising the aforementioned fusion proteins and a pharmaceutically acceptable carrier. Depending on the intended use or mode of administration, solid or liquid pharmaceutically acceptable carriers can be employed in the pharmaceutical composition.

A further aspect of the invention relates to methods for treating a mammal with a disease or condition alleviated by the administration of any of the aforementioned fusion proteins. In one embodiment, the disease or condition is viral infection. In another embodiment, the disease or condition is anemia, while in yet another embodiment, the disease or condition is multiple sclerosis.

Other embodiments and details of the invention are presented herein below.

DETAILED DESCRIPTION

Definitions

Figure 1:
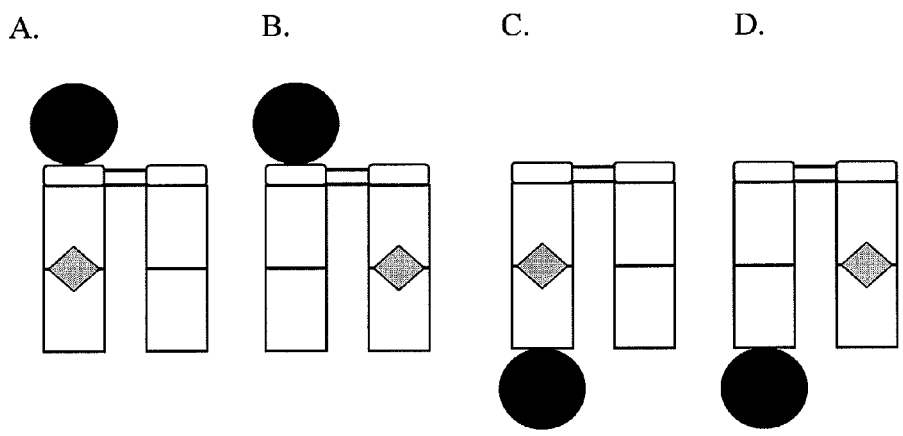
FIGS. 1A-1D schematically illustrate how a biologically active molecule (circle) may be linked to the Fc subunits of an antibody, shown here as a hinge (small rectangle), a CH2 domain and a CH3 domain (large rectangle). One of the Fc subunits includes a mutation in the FcRn binding site (diamond). The biologically active molecule may be linked to the N-terminus (FIGS. 1A and 1B) or the C-terminus (FIGS. 1C and 1D) of the Fc subunit.
Figure 1:
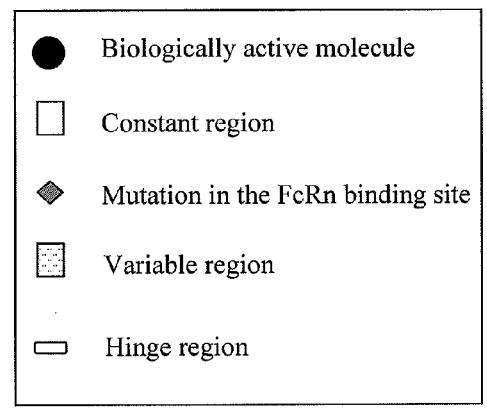
Figure 2:
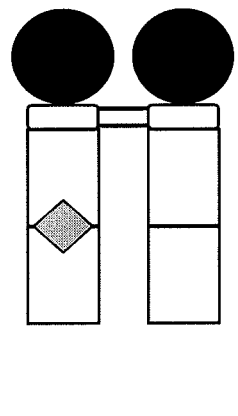
FIGS. 2A-2F illustrate a subset of ways in which two biologically active molecules may be linked to the Fc subunits of an antibody. One of the Fc subunits includes a mutation in the FcRn binding site. The two biologically active molecules may be same or different (black or white circles).
Figure 2:
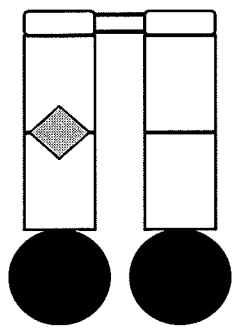
Figure 2:
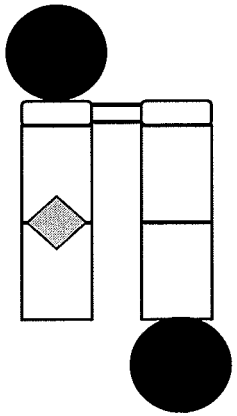
Figure 2:
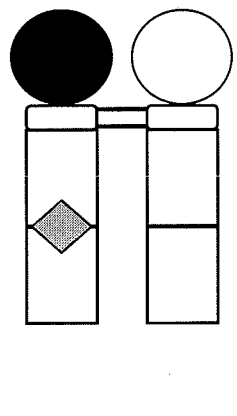
Figure 2:
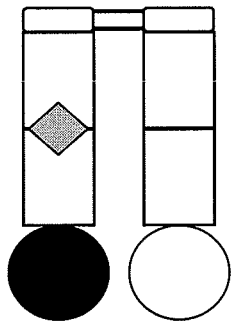
Figure 2:
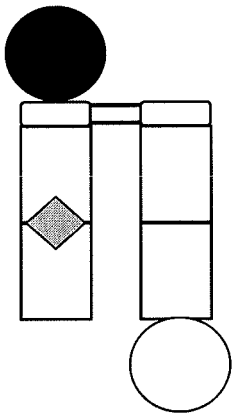
Figure 3:
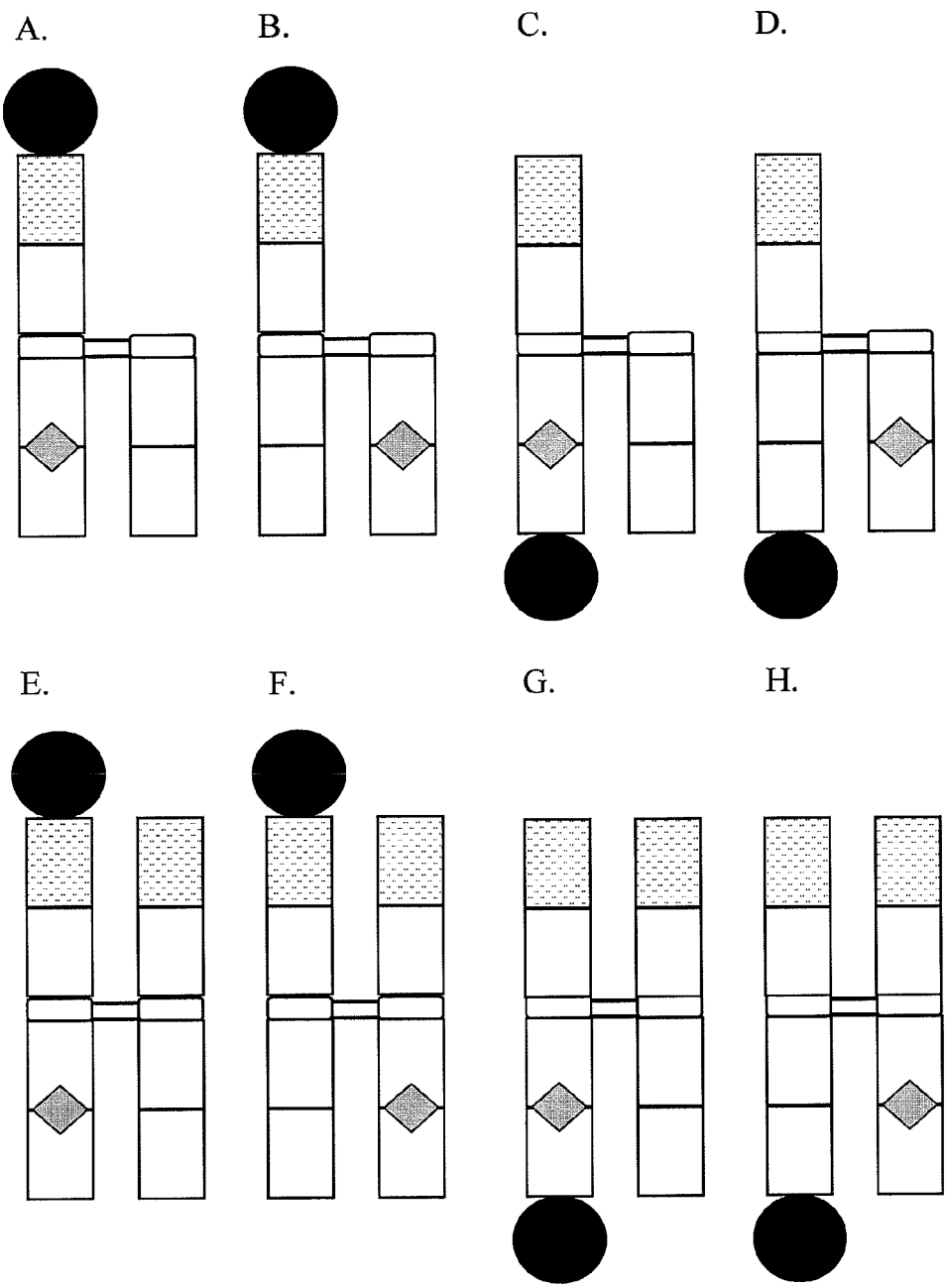
FIGS. 3A-3H show how a biologically active molecule may be linked to an antibody that include a constant region (rectangles) and a variable region (stippled rectangle) of the heavy chain. The antibody fusion protein may include a single variable region (FIGS. 3A-3D), or the antibody fusion protein may include two variable regions (FIGS. 3E-3H). One of the heavy chains includes a mutation in the FcRn binding site.
Figure 4:
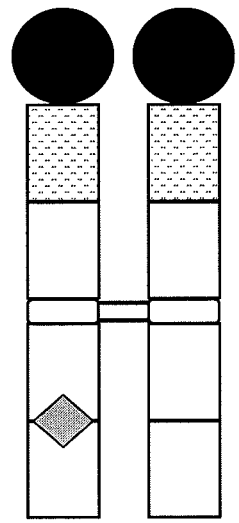
FIGS. 4A-4F show how two biologically active molecules may be linked to an antibody that include a constant region (rectangles) and a variable region (stippled rectangle) of the heavy chain. The two biologically active molecules may be same or different (black or white circles). One of the heavy chains includes a mutation in the FcRn binding site.
Figure 4:
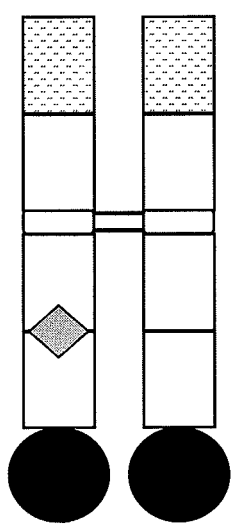
Figure 4:
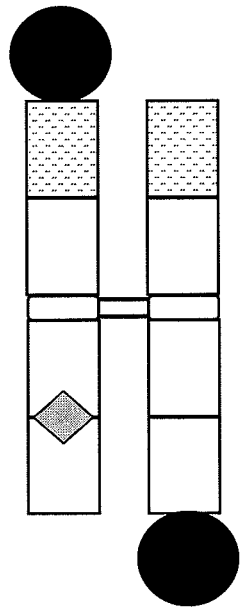
Figure 4:
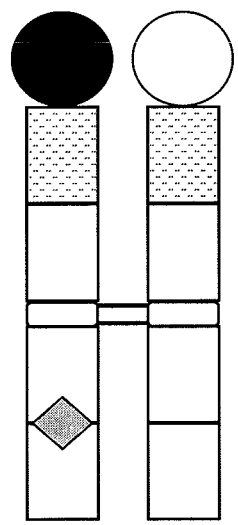
Figure 4:
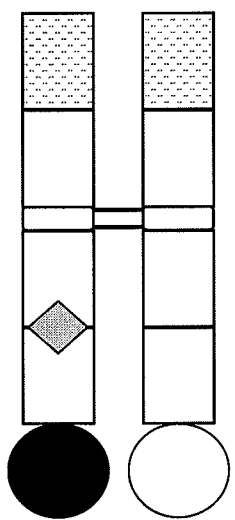
Figure 4:
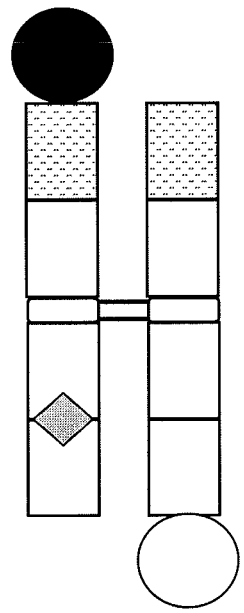
Figure 5:
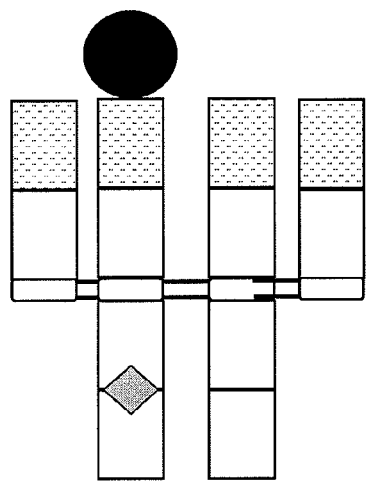
FIGS. 5A-5D show a subset of ways in which a biologically active molecule may be linked to an intact immunoglobulin such as an IgG. The constant regions of the heavy and light chains are shown as rectangles and the variable regions are shown as stippled rectangles. One of the heavy chains includes a mutation in the FcRn binding site. The biologically active molecule may be linked to the heavy chain (FIGS. 5A and 5B) or the light chain (FIGS. 5C and 5D).
Figure 5:
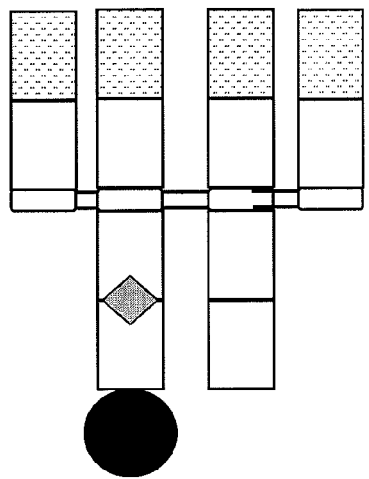
Figure 5:
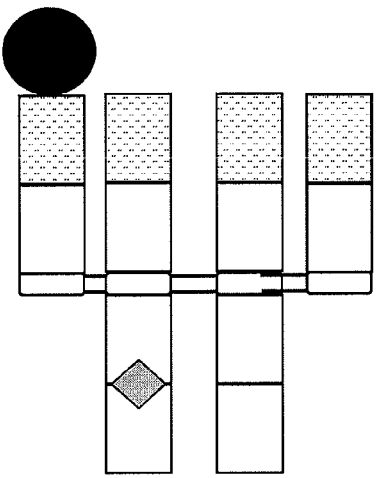
Figure 5:
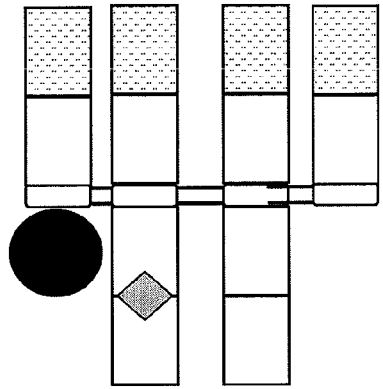
Figure 6:
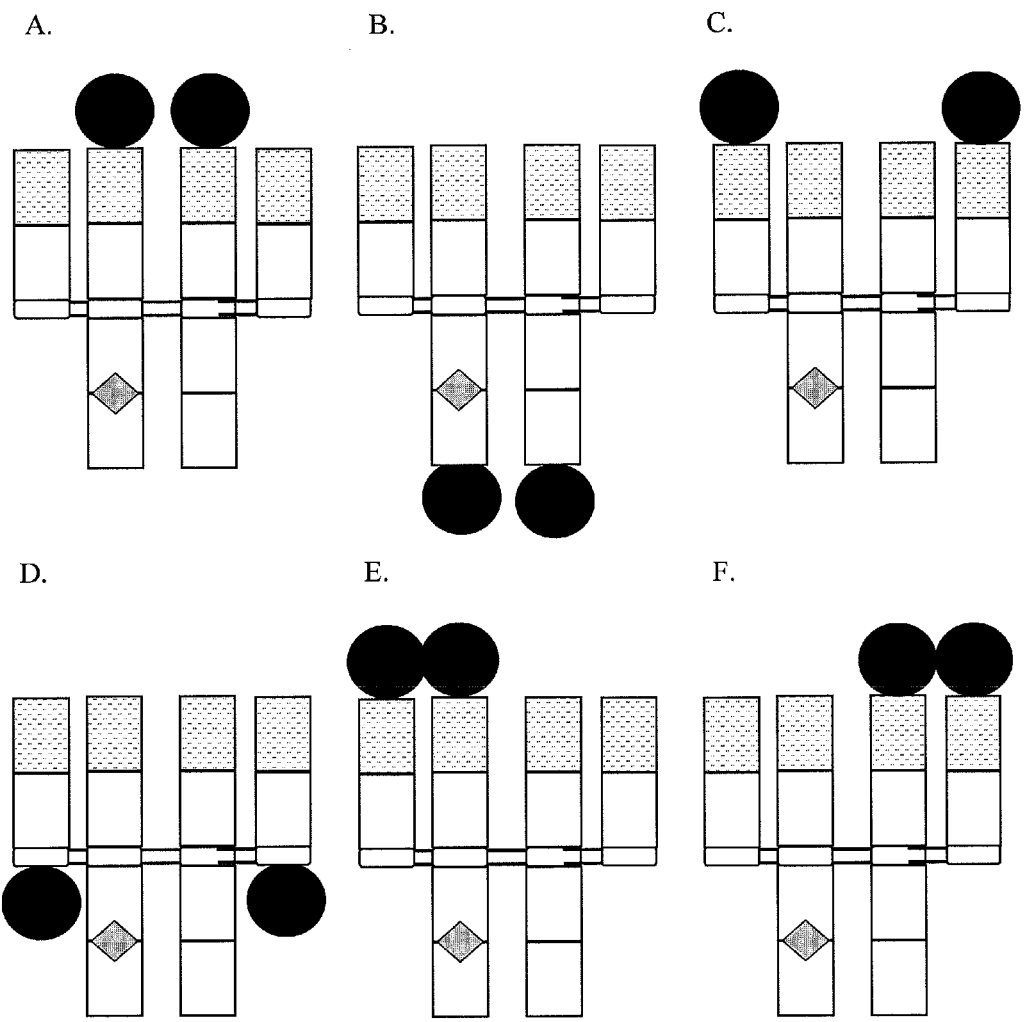
FIGS. 6A-6F illustrate how two biologically active molecules can be linked to an intact immunoglobulin such as an IgG. One of the heavy chains includes a mutation in the FcRn binding site. The biologically active molecules may be linked to the heavy chains (FIGS. 6A and 6B) or the light chains (FIGS. 6C and 6D). Alternatively, one of the biologically active molecule may be linked to the heavy chain and the other biologically active molecule is linked to the light chain (FIGS. 6E and 6F).
Figure 7:
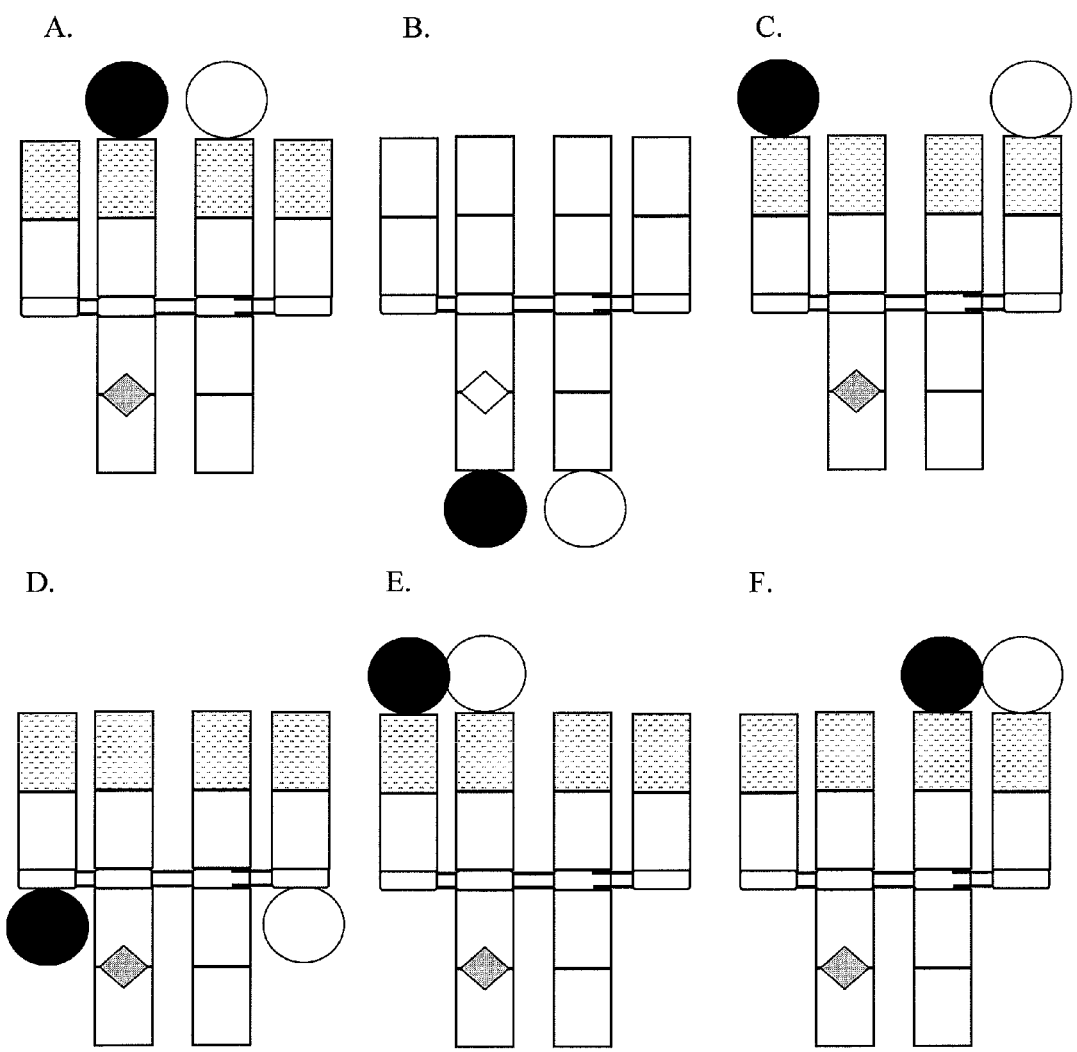
FIGS. 7A-7F illustrate how two different biologically active molecules can be linked to an intact immunoglobulin such as an IgG. One of the heavy chains includes a mutation in the FcRn binding site.

An "effective amount" or "pharmaceutically effective amount" of a therapeutic or composition contemplated herein is an amount sufficient to produce a desired effect, e.g., reducing the severity of disease symptoms. The pharmaceutically effective amount will vary depending upon the subject and disease condition being treated, the weight and age of the subject, the severity of the disease condition, the manner of administration and the like. For example, certain compositions of the present invention may be administered in a sufficient amount to produce a reasonable benefit/risk ratio applicable to such treatment.

The term "nucleic acid" as used herein refers to a polymer containing at least two deoxyribonucleotides or ribonucleotides in either single- or double-stranded form and includes DNA and RNA. DNA may be in the form of, e.g., plasmid DNA, pre-condensed DNA, a PCR product, vectors (P1, PAC, BAC, YAC, artificial chromosomes), expression cassettes, chromosomal DNA, or derivatives and combinations of these groups. RNA may be in the form of mRNA, tRNA, rRNA, tRNA, vRNA, and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide nucleic acids (PNAs). "Nucleotides" contain a deoxyribose (DNA) or ribose (RNA), a sugar, a nitrogenous base, and a phosphate group or analog thereof. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "small molecule" refers to a molecule with a molecular weight of less than 1 kDa. The small molecule can be any of a variety of molecules, naturally occurring or synthetic. The biological active molecule can be a small organic molecule, a small inorganic molecule, a sugar molecule, a lipid molecule, or the like. The small molecule can be a drug.

The term "pharmaceutically acceptable excipient" refers to a pharmaceutically-acceptable material, composition or vehicle, such as a liquid or solid filler, diluent, excipient, or solvent, used in formulating pharmaceutical products. Each excipient must be "acceptable" in the sense of being compatible with the subject composition and its components and not injurious to the patient. Some examples of materials which may serve as pharmaceutically acceptable excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Antibody Fusion Proteins

Antibody fusion proteins linking a protein of interest to an immunoglobulin constant region, for example, an immunoglobulin Fc region, possess both the biological activity of the linked protein as well as the advantages associated with the presence of the immunoglobulin moiety. Such fusion proteins exhibit enhanced stability and increased bioavailability compared to the biologically active molecule alone. Additionally, the presence of the Fc fragment can significantly improve protein production. This is believed to occur, in part, because the Fc moiety of the fusion protein is designed for efficient secretion of the fusion protein, and, in part, because the fusion proteins can be produced in and secreted from host cells that naturally express the immunoglobulin such that the fusion protein is readily secreted from the host cell. Finally, the Fc fragment can further be exploited to aid in the purification of the fused polypeptide.

In adult mammals, FcRn acts as a protective receptor that binds and salvages IgG from degradation. Numerous studies support a correlation between the affinity for FcRn binding and the serum half-life of an antibody. Surprisingly, the present invention provides that antibody fusion proteins with a mutation reducing FcRn binding exhibit comparable biological properties such as prolonged circulating half-life as corresponding fusion proteins without the mutation. Furthermore, given the role of FcRn in IgG mediated opsonization, it is contemplated that the antibody fusion protein with a mutation that reduces affinity for FcRn may exhibit reduced immunogenicity.

Consequently, the present invention provides for antibody fusion proteins comprised of two polypeptide chains. The first polypeptide chain includes a biologically active molecule linked to at least a portion of an immunoglobulin constant region, and the second polypeptide chain includes at least a portion of an immunoglobulin constant region. The amino acid sequence of the portion of the immunoglobulin constant region of one of the polypeptide chains differs from the amino acid sequence of the portion of the immunoglobulin constant region of the second polypeptide chain in that it contains a mutation in the FcRn binding site.

The invention also provides methods and compositions for expressing soluble, biologically active antibody fusion proteins with a mutation in the FcRn binding site that reduces FcRn binding. In particular, the invention provides nucleic acid molecules that encode a polypeptide chain that includes a biologically active molecule and at least a portion of an immunoglobulin constant region comprising a mutation that reduces FcRn binding. In another aspect, the invention relates to a composition of one nucleic acid encoding a polypeptide chain that includes a biologically active molecule and at least a portion of an immunoglobulin constant region, and a second nucleic acid encoding a second polypeptide chain that includes at least a portion of an immunoglobulin constant region. One of the nucleic acid sequences contains a mutation in the FcRn binding site.

The invention also provides methods for treating a disease or condition alleviated by the administration of the antibody fusion proteins by administering to a mammal an effective amount of the antibody fusion protein of the invention.

Antibody Fusion Protein Structural Variants

The invention discloses antibody fusion proteins comprised of two polypeptide chains. The first polypeptide chain includes a biologically active molecule linked to at least a portion of an immunoglobulin constant region, and the second polypeptide chain includes at least a portion of an immunoglobulin constant region. One of the polypeptide chains comprises a mutation in FcRn binding.

FIG. 1 illustrates a subset of ways in which a biologically active molecule may be linked to the immunoglobulin constant region, for example, the Fc subunit, of an antibody. The biologically active molecule can be linked to the N-terminus of the immunoglobulin constant region (FIGS. 1A and 1B) or to the C-terminus of the immunoglobulin constant region (FIGS. 1C and 1D). The biologically active molecule can be linked to the immunoglobulin constant region with a mutation in FcRn binding or linked to the immunoglobulin constant region without the mutation.

The antibody fusion protein can include at least two biologically active molecules. As illustrated in FIG. 2, the biologically active molecules may be linked to the N-terminus of the immunoglobulin constant region (FIG. 2A) or to the C-terminus of the immunoglobulin constant region (FIG. 2B), or one of the biologically active molecule can be linked to the N-terminus of the immunoglobulin constant region and the second biologically active molecule linked to the C-terminus of the immunoglobulin constant region (FIG. 2C). The two biologically active molecules may be the same or different. FIGS. 2D-2F illustrate how two different biologically active molecules can be linked to the immunoglobulin constant regions.

The invention also features antibody fusion proteins comprised of two polypeptide chains, wherein at least one of the peptide chains comprise an antibody variable domain. FIG. 3 illustrates a subset of ways in which a biologically active molecule can be linked to immunoglobulin regions comprised of an antibody variable domain. The biologically active molecule can be linked to either the N-terminus or the C-terminus of one of the polypeptide chains comprised of an antibody variable domain (FIGS. 3A-3D). Alternatively, both peptide chains can comprise an antibody variable domain (FIGS. 3E-3H).

FIG. 4 shows how two biologically active molecules can be linked to an antibody that include a constant region and a variable region of the heavy chain. The biologically active molecule can be linked to the N-terminus, the C-terminus, or the N-terminus and C-terminus of the immunoglobulin regions (FIGS. 4A-4C). Different biologically active molecules can be linked to the immunoglobulin regions (FIGS. 4D-4F).

The fusion protein of the invention can include a biologically active molecule linked to an intact antibody, for example, an IgG. FIG. 5 depicts a subset of ways in which a biologically active molecule can be linked to an antibody. The biologically active molecule can be linked to the N-terminus or the C-terminus of the immunoglobulin heavy chain (FIGS. 5A and 5B). Alternatively, the biologically active molecule can be linked to the N-terminus or the C-terminus of the immunoglobulin light chain (FIGS. 5C and 5D).

FIG. 6 illustrates how two biologically active molecules can be linked to an intact antibody. The biologically active molecules can be linked to the N-terminus or the C-terminus of the immunoglobulin heavy chain (FIGS. 6A and 6B). Alternatively, the biologically active molecule can be linked to the N-terminus or the C-terminus of the immunoglobulin light chain (FIGS. 6C and 6D). One of the biologically active molecules can be linked to the immunoglobulin heavy chain, and the second biologically active molecule can be linked to the immunoglobulin light chain (FIGS. 6E and 6F). FIG. 7 shows how different biologically active molecules can be linked to the intact antibody (FIGS. 7A-7F).

Antibody Fusion Protein Biological Properties

As mentioned previously, antibody fusion proteins of the invention can demonstrate comparable biological properties such as prolonged circulating half-life as corresponding fusion proteins without the mutation. For example, FIGS. 11 to 16 demonstrate that human Fcγ4-IFNβ with the H435A mutation displayed similar serum stability as human Fcγ4-IFNβ without the mutation in vivo. Fcγ4-IFNβ with the H435A mutation intravenously injected into mice exhibited similar circulating half-life as antibody fusion proteins without the mutation (FIGS. 11 and 12). Similarly Fcγ4-IFNβ with the H435A mutation injected subcutaneously into mice exhibited similar circulating half-life as antibody fusion proteins without the mutation (FIGS. 14 and 15).

Derivatives of the antibody fusion proteins of the invention are contemplated and can be made by altering their amino acid sequences by substitutions, additions, and/or deletions/truncations or by introducing chemical modifications that result in functionally equivalent molecules. It will be understood by one of skill in the art that certain amino acids in a sequence of any protein may be substituted for other amino acids without adversely affecting the activity of the protein. Derivatives, analogs or mutants resulting from such changes and the use of such derivatives are within the scope of the present invention.

FcRn Binding Site Mutations

The present invention provides antibody fusion proteins with a mutation in the FcRn binding site of one polypeptide chain comprising the Fc. While the other polypeptide chain comprising the Fc retains the intrinsic binding affinity to FcRn, the mutation results in reduced binding avidity of the antibody fusion protein to the FcRn receptor. Reduced binding is characterized by low affinity with an affinity constant $K_A$ of lower than $10^6$ $M^{-1}$. If necessary, FcRn binding can be reduced by varying the binding conditions. Binding conditions such as the concentration of the molecules, ionic strength of the solutions, temperature, time allowed for binding can be determined by one skilled in the art.

The region of the Fc portion of IgG that binds to the FcRn receptor has been described based on X-ray crystallography (Burmeister et al., 1994, *Nature* 372:379). IgG residues that are involved in binding to FcRn are located at the CH2-CH3 domain interface of the Fc region. The major contact sites include amino acid residues 248, 250-257, 272, 285, 288, 290, 291, 308-311, and 314 of the CH2 domain and amino acid residues 385-387, 428, and 433-436 of the CH3 domain.

Using this knowledge, the Fc fragment of the antibody fusion protein can be modified according to well recognized procedures such as site-directed mutagenesis to generate modified antibody fusion proteins with reduced affinity for FcRn. The modifications can be substitutions, additions, and/or deletions/truncations. For example, the immunoglobulin constant region of the antibody fusion protein may contain an alteration at position 435, corresponding to a histidine in the native IgG1 Fc fragment. The amino acid alteration may replace the histidine with alanine (H435A) through methods known in the art.

In addition to an alteration at position 435, the invention also contemplates antibody fusion proteins with other altered residues. For example, the antibody fusion protein may be altered at one or more of positions 233, 234, 235, 236, 253, 254, 255, 288, 415, 433, 435, and 436. Examples of modifications that reduce or abrogate binding to FcRn include, but are not limited to, the following: E233A, L234A, L235A, G236A, I253A, S254A, R255A, K288A, S415A, H433A, H435A, Y436A. It is contemplated that additional amino acid residues not listed above may also be mutated to reduce FcRn binding. Furthermore, in addition to alanine, other amino acid residues may be substituted for the wild type amino acids at the positions specific above. The mutations may be introduced singly, or combinations of two, three or more of such mutations may be introduced together. Furthermore, one of the polypeptide chains of the antibody fusion protein may be mutated to reduce FcRn binding or both polypeptide chains may be mutated. Any of the mutations described herein can be used regardless of the biologically active molecule.

Immunoglobulin Regions

The antibody fusion protein of the invention includes at least a portion of an immunoglobulin constant region. Intact immunoglobulins include four protein chains that associate covalently—two heavy chains and two light chains. Each chain is further comprised of one variable region and one constant region. Depending upon the immunoglobulin isotype, the heavy chain constant region contains 3 or 4 constant region domains (e.g. CH1, CH2, CH3, CH4) and a hinge region. The domains are named sequentially as follows: CH1-hinge-CH2-CH3(-CH4).

The portion of an immunoglobulin constant region can include a portion of an IgG, an IgA, an IgM, an IgD, or an IgE. In one embodiment, the immunoglobulin is an IgG. In another embodiment, the immunoglobulin is IgG1. In another embodiment, the immunoglobulin is IgG2. In another embodiment, the immunoglobulin is IgG3, while in yet another embodiment, the immunoglobulin is IgG4. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of one skilled in the art.

The portion of an immunoglobulin constant region can include the entire heavy chain constant region, or a fragment or analog thereof. In one embodiment, the portion of an immunoglobulin constant region is an Fc fragment. For example, an immunoglobulin Fc fragment may include 1) a CH2 domain; 2) a CH3 domain; 3) a CH4 domain; 4) a CH2 domain and a CH3 domain; 5) a CH2 domain and a CH4 domain; 6) a CH3 domain and a CH4 domain; or 7) a combination of an immunoglobulin hinge region and/or a CH2 domain and/or CH3 domain and/or a CH4 domain. In one embodiment, the immunoglobulin Fc region includes at least an immunoglobulin hinge region, while in another embodiment the immunoglobulin Fc region includes at least one immunoglobulin constant heavy region, for example, a CH2 domain or a CH3 domain, and depending on the type of immunoglobulin used to generate the Fc region, optionally a CH4 domain. In another embodiment, the Fc region includes a hinge region, a CH2 domain and a CH3 domain, and preferably lacks the CH1 domain, while in another embodiment, the Fc region includes a hinge region and a CH2 domain. In yet another embodiment, the Fc region includes a hinge region and a CH3 domain.

The immunoglobulin Fc fragment may be from any immunoglobulin class. For example, the immunoglobulin class may be IgG (IgG γ1) (γ subclasses 1, 2, 3, or 4). Other classes of immunoglobulin such as IgA (Igα), IgD (Igδ), IgE (Igε), and IgM (Igμ), can also be used. The choice of appropriate immunoglobulin heavy chain constant regions is discussed in detail in U.S. Pat. Nos. 5,541,087, and 5,726,044. It is understood that a person skilled in the art will know how to choose the particular immunoglobulin heavy chain constant region from certain immunoglobulin classes and subclasses to achieve a particular result.

It is contemplated that the Fc fragment used in the generation of the fusion proteins can be adapted to the specific applications. For example, the Fc fragment can be derived from an immunoglobulin γ1 isotype or variants thereof. The use of human γ1 as the Fc fragment sequence has several advantages. For example, an Fc fragment derived from an immunoglobulin γ1 isotype can be used when targeting the fusion protein to the liver is desired. Additionally, if the antibody fusion protein is to be used as a biopharmaceutical, the Fcγ1 domain may confer effector function activities to the fusion protein. The effector function activities include the biological activities such as placental transfer and increased serum half-life. The immunoglobulin Fc fragment also provides for detection by anti-Fc ELISA and purification through binding to *Staphylococcus aureus* protein A ("Protein A").

Alternatively, the Fc fragment of the antibody fusion protein is derived from an immunoglobulin γ4 isotype. Because the immunoglobulin γ4 isotype is ineffective in mediating effector functions and displays vastly reduced binding to Fcγ receptor, it is contemplated that the antibody fusion proteins with immunoglobulin γ4 as the Fc region may exhibit reduced immune effector functions and enhanced circulating half-life when administered to a mammal.

The immunoglobulin Fc fragment may combine multiple immunoglobulin classes or subclasses. For example, the fragment may combine an IgG1 hinge region and IgG2 CH2 and CH3 domain (see, e.g., U.S. Pat. No. 7,148,326). In some embodiments, portions of a domain are combined from different isotypes to create a strand exchange engineered domain ("SEED") with altered dimerization properties, as described in U.S. Patent Application Publication No. 2007/0287170.

In one embodiment, the antibody fusion protein includes at least one antibody variable domain. The antibody variable domain may be heavy chain variable domain or light chain variable domain.

It is understood that portions of an immunoglobulin constant region for use in the present invention can include mutants or analogs thereof, or can include chemically modified immunoglobulin constant regions (e.g. pegylated), or fragments thereof. A person skilled in the art can prepare such variants using well-known molecular biology techniques.

Biologically Active Molecules

The invention relates to antibody fusion proteins that include two polypeptide chains. The first polypeptide chain includes a biologically active molecule linked to at least a portion of an immunoglobulin constant region, and the second polypeptide chain includes at least a portion of an immunoglobulin constant region. The biologically active molecule may be linked to the amino-terminus of the immunoglobulin constant region. Alternatively, the biologically active molecule may be linked to the carboxy terminus of the immunoglobulin constant region. In an embodiment, the second polypeptide chain may also include a biologically active molecule.

The invention contemplates the use of any biologically active molecule capable of exerting a biological effect when administered to a mammal. The biologically active molecule can include but is not limited to polypeptides, nucleic acids, small molecules. Other examples of biologically active molecules include but are not limited to hormones, antiviral agents, hemostatic agents, peptides, proteins, chemotherapeutics, vitamins, co-factors, nucleosides, nucleotides, oligonucleotides, enzymatic nucleic acids, antisense nucleic acids, triplex forming oligonucleotides, and aptamers.

Cytokines

In one embodiment, the biologically active molecule is a cytokine. Cytokines are factors that support the growth and maturation of cells, including lymphocytes. Examples of cytokines include, but are not limited to, interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, lymphokine inhibitory factor, macrophage colony stimulating factor, platelet derived growth factor, stem cell factor, tumor necrosis factor, granulocyte colony stimulating factor, and granulocyte macrophage colony stimulating factor.

In a specific embodiment, the biologically active molecule can include human interferons, for example, interferon-β. The interferon-β moiety can be a wild-type mature human interferon-β protein, or a sequence at least 60%, 65%, 70%, 75%, 80%, 85%, 90%, or 95% identical to wild-type mature human interferon-β. For example, the biologically active molecule can incorporate a human interferon-β moiety with one or more mutations, e.g. to improve the protein folding properties of the fusion protein, to reduce aggregation, or to improve protein expression. For example, the interferon-β moiety of the antibody fusion protein can contain alterations at one, two, three, four, or more of positions 17, 50, 57, 130, 131, 136, and 140 corresponding to the native mature interferon-β. The amino acid alterations at these positions can be generated by amino acid substitutions, amino acid deletions, or amino acid modifications through methods known in the art. Alterations introduced at these residues are believed to alleviate non-covalent aggregation. In one example, the cysteine at position 17 is substituted with either a serine (C17S), an alanine (C17A), a valine (C17V), or a methionine (C17M). In some embodiments, the phenylalanine at position 50 is replaced with histidine (F50H). In some embodiments, the leucine at position 57 is replaced by alanine (L57A), while in other embodiments, the leucine at position 130 is replaced by alanine (L130A). In some embodiments, the histidine at position 131 is replaced by alanine (H131A), while in other embodiments the lysine at position 136 is replaced by alanine (K136A). In some embodiments, the histidine at position 140 is replaced with either an alanine (H140A) or threonine (H140T). While certain amino acid substitutions have been enumerated, the invention is not limited to these alterations. Any suitable amino acid capable of conferring the appropriate properties on the fusion protein may be substituted in place of the original amino acid residues at positions 17, 50, 57, 130, 131, 136, and 140 of the native mature interferon-β. The present invention also contemplates an interferon-β moiety of the antibody fusion protein having a combination of one, two, three, four, five, six, or seven of the alterations at positions 17, 50, 57, 130, 131, 136, and 140 as disclosed herein.

Growth Factors

In one embodiment, the biologically active agent is a growth factor. The biologically active molecule can be any agent capable of inducing cell growth and proliferation. Examples of growth factors include, but are not limited to, hepatocyte growth factor, fibroblast growth factor, keratinocyte growth factor, nerve growth factor, tumor growth factor-α, epidermal growth factor, VEGF, insulin growth factor, and insulin-like growth factor I and II.

In a specific embodiment, the biologically active molecule is any agent that can induce erythrocytes to proliferate. Thus one example of a biologically active molecule contemplated by the invention is human erythropoietin.

Hormones

In one embodiment, the biologically active molecule is a hormone. Hormones alter cell growth, function, and metabolism. Examples of hormones include, but are not limited to, pituitary hormones, e.g., chorionic gonadotropin, cosyntropin, menotropins, somatotropin, iorticotropin, protirelin, thyrotropin, vasopressin, lypressin; adrenal hormones, e.g., beclomethasone dipropionate, betamethasone, dexamethasone, triamcinolone; pancreatic hormones, e.g., glucagon, insulin; parathyroid hormone, e.g., dihydrochysterol; thyroid hormones, e.g., calcitonin, thyroglobulin, teriparatide acetate; steroid hormones, e.g., glucocorticoids, estrogens, progestins, androgens, tetrahydrodesoxycaricosterone; gastrointestinal hormones: cholecystokinin, enteroglycan, galanin, gastrins, pentagastrin, tetragastrin, motilin, peptide YY, and secretin. In a specific embodiment, the biologically active molecule is human growth hormone.

Nucleic Acids

In one embodiment, the biologically active molecule is a nucleic acid such as DNA or RNA. For example, the biologically active molecule can be a nucleic acid molecule that is used in RNA interference such as antisense RNA, short interfering RNA (siRNA), double-stranded RNA (dsRNA), micro-RNA (miRNA), and short hairpin RNA (shRNA). The nucleic acid molecule should be about 6 to about 60 nucleotides in length. For example, in some embodiments, the nucleic acid molecule is about 15 to about 50, about 25 to about 45, or about 30 to about 40 nucleotides in length.

The oligonucleotides can be DNA or RNA or mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as polypeptides (e.g. for targeting host cell receptors in vivo), or agents facilitating transport across the cell membrane (see, e.g., Letsinger et al. (1989) *Proc. Natl. Acad. Sci. USA* 86:6553; Lemaitre et al. (1987) *Proc. Natl. Acad. Sci. USA* 84:648; and WO 88/09810) or the blood-brain barrier (see, e.g., WO 89/10134), hybridization-triggered cleavage agents (see, e.g., Krol et al. (1988) *BioTechniques* 6:958) or intercalating agents (see, e.g., Zon (1988) *Pharm. Res.* 5:539). To this end, the oligonucleotide may be conjugated to another molecule, e.g., a polypeptide, hybridization triggered cross-linking agent, transport agent, or hybridization-triggered cleavage agent.

Small Molecules

The invention also contemplates the use of any therapeutic small molecule or drug as the biologically active molecule. The biologically active molecule can be, for example, a lipid molecule. The biologically active molecule can be a sugar molecule. The biologically active molecule can be a small organic molecule or a small inorganic molecule.

Production of Modified Antibody Fusion Proteins

It is understood that the present invention can exploit conventional recombinant DNA methodologies to generate the antibody fusion proteins useful in the practice of the invention. The antibody fusion constructs preferably are generated at the DNA level, and the resulting DNAs integrated into expression vectors, and expressed to produce the fusion proteins of the invention.

The invention provides nucleic acids encoding a biologically active molecule linked to at least a portion of an immunoglobulin constant region comprising a mutation in the FcRn binding site. In one embodiment, the mutation is a codon substitution replacing the histidine at position 435 of the immunoglobulin constant region with an alanine (H435A). The invention also provides compositions of nucleic acids: the first nucleic acid encodes a biologically active molecule and at least a portion of an immunoglobulin constant region; the second nucleic acid encodes at least a portion of an immunoglobulin constant region. One of the nucleic acids encodes an immunoglobulin constant region with a mutation affecting FcRn binding. In one embodiment, the mutation is a codon substitution replacing the histidine at position 435 of the immunoglobulin constant region with an alanine (H435A). The nucleic acids can also include additional sequences or elements known in the art (e.g., promoters, enhancers, poly A sequences, or affinity tags).

Nucleic acids and nucleic acid compositions according to the invention can be readily synthesized using recombinant techniques well known in the art. For example, nucleic acids can be synthesized by standard methods, e.g., by use of an automated DNA synthesizer.

For recombinant protein production, the nucleic acid or the nucleic acid composition is inserted into appropriate expression vehicles, i.e. vectors which contains the necessary elements for the transcription and translation of the inserted coding sequence. As used herein, the term "vector" is understood to mean any nucleic acid including a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include a retrovirus, an adenovirus and an adeno-associated virus.

A useful expression vector is pdCs (Lo et al. (1988) *Protein Engineering* 11:495), which transcription utilizes the enhancer/promoter of the human cytomegalovirus and the SV40 polyadenylation signal. The enhancer and promoter sequence of the human cytomegalovirus used is derived from nucleotides −601 to +7 of the sequence provided in Boshart et al. (1985) *Cell* 41:521. The vector also contains the mutant dihydrofolate reductase gene as a selection marker (Simonsen and Levinson (1983) *Proc. Nat. Acad. Sci. USA* 80:2495).

An appropriate isolated host cell can be transformed or transfected with the DNA sequence of the invention, and utilized for the expression and/or secretion of the target protein. Exemplary isolated host cells for use in the invention include immortal hybridoma cells, NS/0 myeloma cells, 293 cells, Chinese hamster ovary cells, HeLa cells, and COS cells.

Methods of Using the Antibody Fusion Proteins

The invention also provides pharmaceutical compositions comprising the antibody fusion protein with a mutation in the FcRn binding site and a pharmaceutically acceptable carrier or excipient. The term "pharmaceutically acceptable excipient" is art-recognized and refers to a pharmaceutically-acceptable material, composition or vehicle, such as a liquid or solid filler, diluent, excipient, or solvent, used in formulating pharmaceutical products. Each excipient must be "acceptable" in the sense of being compatible with the subject composition and its components and not injurious to the patient. Examples of suitable pharmaceutical carriers are described in Remington's Pharmaceutical Sciences by E. W. Martin. Examples of excipients can include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Compositions of the present invention may be administered by any route which is compatible with the particular molecules. It is contemplated that the compositions of the present invention may be provided to a mammal by any suitable means, directly (e.g., locally, as by injection, implantation or topical administration to a tissue locus) or systemically (e.g., parenterally or orally). Where the composition is to be provided parenterally, such as by intravenous, subcutaneous, ophthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the composition preferably includes part of an aqueous or physiologically compatible fluid suspension or solution. Thus, the carrier or vehicle is physiologically acceptable so that in addition to delivery of the desired composition to the patient, it does not otherwise adversely affect the patient's electrolyte and/or volume balance. The fluid medium for the agent thus can include normal physiologic saline.

The present invention provides methods of treating various cancers, viral diseases, other diseases, related conditions and causes thereof by administering the DNA, RNA or proteins of the invention to a mammal having such condition. Related conditions may include, but are not limited to inflammatory conditions or an autoimmune disease, such as multiple sclerosis, arthritis, psoriasis, lupus erythematosus; a variety of malignancies, such as acute myeloid leukemia, multiple myeloma, Hodgkin's disease, basal cell carcinoma, cervical dysplasia and osteosarcoma; a variety of viral infections, including viral hepatitis, herpes zoster and genitalis, papilloma viruses, viral encephalitis, and cytomegalovirus pneumonia; anemia; and hemostatic disorders.

The optimal dose of the fusion protein of the invention will depend upon the disease being treated and upon the existence of side effects. The optimal dosages can be determined using routine experimentation. Dosages per administration can range from 0.1 mg/m$^2$-100 mg/m$^2$, 1 mg/m$^2$-20 mg/m$^2$, and 2 mg/m$^2$-6 mg/m$^2$. Administration of the fusion protein may be by periodic bolus injections, or by continuous intravenous or intraperitoneal administration from an external reservoir (for example, from an intravenous bag) or internal (for example, from a bioerodable implant). Furthermore, it is contemplated that the fusion proteins of the invention also may be administered to the intended recipient together with a plurality of different biologically active molecules. It is contemplated, however, that the optimal combination of fusion protein and other molecules, modes of administration, dosages may be determined by routine experimentation well within the level of skill in the art.

It is contemplated that the antibody fusion protein of the invention can also be used to treat a mammal with a disease or condition in combination with at least one other known agent to treat said disease or condition.

EXAMPLES

Example 1

Construction of DNA Sequences for the Expression of huFcγ4h-mono-L-DI-IFNβ

The huFcγ4h-mono-L-DI-IFNβ (huFcγ4 hinge mutant-linker monomeric de-immunized interferon-β) antibody fusion protein is a heterodimer consisting of a human Fcγ4h chain and a human Fcγ4h-Linker-DI-IFNβ chain. The protein was produced in mammalian cells by coexpressing the human Fcγ4h chain and the human Fcγ4h-Linker-DI-IFNβ chain, the transcription units of which were contained in one single plasmid or two separate plasmids.

The DNA encoding the huFcγ4h (huFcγ4 hinge mutant) was derived from the human IgG4 genomic sequence and then engineered to contain a modified γ1 hinge region in order to minimize half-molecule formation. The formation of IgG4 half molecules that did not form covalent disulphide bonds at the hinge regions was previously reported (Angal et al. (1993) *Mol. Immunol.* 30:105).

Construction of DNA Sequence Encoding the Fc Fragment of the Human Immunoglobin-Gamma 4 (Fcγ4)

The genomic sequence encoding human IgG4 was obtained from cellular DNA isolated from HeLa cells. The sequence is highly conserved with the published IgG4 sequence—Locus HUMIGCD2 (Accession K01316) in GenBank, except for the difference of 3 amino acid residues in the CH3 region. The published sequence contains R409, E419, V422, whereas our sequence contains K409, Q419, I422. Interestingly, K409 and Q419 are also found in human IgG1, IgG2 and IgG3; and I422 is found in human IgG3. Such allotypic determinants consisting of amino acid substitutions from other IgG subclasses are known as isoallotypes, and isoallotypes of the human IgG4 gene have previously been reported (Brusco et al. (1998) *Eur. J. Immunogenetics* 25:349-355). The amino acid sequence of the Fcγ4 fragment is shown in SEQ ID NO: 1.

SEQ ID NO: 1: Peptide Sequences of the huFcγ4 (γ4 Hinge Region Underlined, and K409, Q419, I422 in bold)

ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSKLTVDKSRWQ

QGNIFSCSVMHEALHNHYTQKSLSLSPGK

Modification of the Hinge Region of Fcγ4

The γ4 hinge region with the amino acid sequence "ESKYGPPCPSCP" (SEQ ID NO: 7) was replaced by a modified γ1 hinge region with the amino acid sequence "EPKSSDKTHTCPPCP" (SEQ ID NO: 8) (Lo et al. (1998) *Protein Engineering* 11:495-500) to minimize the formation of half-molecules (U.S. Pat. No. 7,148,321).

In order to modify the hinge region of Fcγ4, the AflII-StuI fragment 5'

(SEQ ID NO: 9)
CTTAAGCGAGTCCAAATATGGTCCCCCATGCCCATCATGCCCAG containing the native γ4 hinge exon (bold) was replaced by the corresponding AflII-StuI fragment 5'-CTTAAGCGAGCCCAAATCT<u>TCT</u>GACAAAACTCACACATGCCCACCGTGCCCAG (SEQ ID NO: 10) containing the modified γ1 hinge exon (bold) with a Cys to Ser substitution (underlined) that eliminates the Cys residue that normally pairs with the light chain. Since the StuI sites in both the γ1 and γ4 exons are C-methylated and the StuI restriction endonuclease is methylation sensitive, both plasmids had to be isolated from a DNA cytosine methylase (DCM) negative strain of bacteria before they could be digested with the StuI enzyme. The resulting Fcγ4 with the modified γ1 hinge region was designated Fcγ4h (γ4h: gamma-4 hinge mutant).

Cloning and De-Immunization of IFN-β

The coding sequence for mature IFN-β was PCR amplified from human placental DNA (Sigma, Poole, UK). The cloned PCR products were sequenced to identify an IFN-β clone, the amino acid sequence of which completely matches with the published wild type IFN-β sequence—Locus XM_005410 in GenBank.

The de-immunized IFN-β (DI-IFNβ) contains three amino acid substitutions (L57A, H131A, H140A) to remove potential T helper cell epitopes and one amino acid substitution (C17S) to minimize covalent aggregation. The DNA encoding DI-IFNβ was cloned into the mammalian expression vector pdCs-huFc (Lo et al. (1998) *Protein Engineering* 11:495-500), which had been modified such that the IFN-β sequence is fused to the C-terminus of human Fcγ4h via a 15 amino acid flexible linker with the amino acid sequence G$_4$SG$_4$SG$_3$SG (SEQ ID NO: 14). The linker-DI-IFNβ was denoted as L-DI- IFNβ, the sequence of which is shown in SEQ ID NO: 2 (linker underlined, and C17S, L57A, H131A, and H140A in bold).

SEQ ID NO: 2: Peptide Sequences of L-DI-IFNβ

GGGGSGGGGSGGGSGMSYNLLGFLQRSSNFQSQKLLWQLNGRLEYCLKDR

MNFDIPEEIKQLQQFQKEDAAATIYEMLQNIFAIFRQDSSSTGWNETIVE

NLLANVYHQINHLKTVLEEKLEKEDFTRGKLMSSLHLKRYYGRILAYLKA

KEYSACAWTIVRVEILRNFYFINRLTGYLRN

Adaptation of a Genomic Leader as the Signal Peptide for Secretion

A genomic signal peptide sequence (438-bp) from a mouse immunoglobulin light chain gene was used for the secretion of both the huFcγ4h and huFcγ4h-L-DI-IFNβ chains. The gene sequence encoding the −2 amino acid residue (the −1 amino acid being the C-terminal residue of the signal peptide) of the signal peptide was mutagenized from a serine residue to a leucine residue (AGC to TTA) so that the DNA encoding the end of the signal peptide is CTTAAGC, where CTTAAG is a created AflII site (Lo et al. (1998) *Protein Engineering* 11:495-500). In addition, the Kozak consensus sequence CCACCATGG was introduced for optimal ribosome binding for translation initiation at ATG (Kozak et al. (1986) *Cell* 44:283-292). This was achieved by mutating the first amino acid residue after the initiation codon from AAG to GAG to give the sequence TCTAGA<u>CCACCATGG</u>AG (SEQ ID NO: 11), where the Kozak consensus sequence is underlined and TCTAGA is an XbaI site. Therefore, the signal peptide contains a substitution at the first amino acid residue after the initiation codon and another substitution at the amino acid residue at the −2 position. Since the signal peptide is cleaved off by signal peptidase inside the cell and does not appear in the secreted protein, these mutations do not affect the amino acid composition of the Fcγ4h and Fcγ4h-L-DI-IFNβ products.

The Peptide and DNA Sequences of the huFcγ4h and huFcγ4h-L-DI-IFNβ Chains

The coding regions for the entire huFcγ4h and huFcγ4h-L-DI-IFNβ chains were completely sequenced. The peptide and DNA sequences of the huFcγ4h and huFcγ4h-L-DI-IFNβ chains are shown and SEQ ID NO: 3 to SEQ ID NO: 6. In order to facilitate ligation of the DNA fragments encoding huFcγ4h and L-DI-IFNβ, a SmaI site was created by using the PGK sequence (Lo et al. (1998) *Protein Engineering* 11:495-500) found in human IgG4 (Locus CAC20457 in GenPept), and also in IgG1 and IgG2; in addition, a lysine to alanine substitution at the C-terminal residue of CH3 was introduced to minimize potential cleavage at the junction. Importantly, the resultant sequence at the CH3-L-DI-IFNβ junction does not create any potential T cell epitope.

SEQ ID NO: 3: Peptide Sequence of the huFcγ4h (Signal Peptide Underlined)

<u>MELPVRLLVLMFWIPASLS</u>EPKSSDKTHTCPPCPAPEFLGGPSVFLFPPK

PKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTPP

VLDSDGSFFLYSKLTVDKSRWQQGNIFSCSVMHEALHNHYTQKSLSLSPGK

SEQ ID NO: 4: DNA Sequence of the huFcγ4h Chain from the Translation Initiation Codon to the Translation Stop Codon (Coding Sequence in Upper Case and Non-Coding Sequence in Lower Case)

ATGGAGTTGCCTGTTAGGCTGTTGGTGCTGATGTTCTGGATTCCTGgtga ggagagagggaagtgagggaggagaatggacagggagcaggagcactgaa tcccattgctcattccatgtattctggcatgggtgagaagatgggtctta tcctccagcatggggcctctggggtgaatacttgttagagggaggttcca gatgggaacatgtgctataatgaagattatgaaatggatgcctgggatgg tctaagtaatgcctagaagtgactagacacttgcaattcactttttttgg taagaagagatttttaggctataaaaaaatgttatgtaaaaataaacatc acagttgaaataaaaaaaaatataaggatgttcatgaattttgtgtataa ctatgtatttctctctcattgtttcagCTTCCTTAAGCGAGCCCAAATCT TCTGACAAAACTCACACATGCCCACCGTGCCCAGgtaagccagcccaggc ctcgccctccagctcaaggcgggacaggtgcccta gagtagcctgcatcc agggacaggccccagccgggtgctgacgcatccacctccatctcttcctc agCACCTGAGTTCCTGGGGGGACCATCAGTCTTCCTGTTCCCCCCAAAAC

CCAAGGACACTCTCATGATCTCCCGGACCCCTGAGGTCACGTGCGTGGTG

GTGGACGTGAGCCAGGAAGACCCCGAGGTCCAGTTCAACTGGTACGTGGA

TGGCGTGGAGGTGCATAATGCCAAGACAAAGCCGCGGGAGGAGCAGTTCA

ACAGCACGTACCGTGTGGTCAGCGTCCTCACCGTCCTGCACCAGGACTGG

CTGAACGGCAAGGAGTACAAGTGCAAGGTCTCCAACAAAGGCCTCCCGTC

CTCCATCGAGAAAACCATCTCCAAAGCCAAAGgtgggacccacggggtgc gagggccacatggacagaggtcagctcggcccaccctctgccctgggagt gaccgctgtgccaacctctgtccctacagGGCAGCCCCGAGAGCCACAGG

TGTACACCCTGCCCCCATCCCAGGAGGAGATGACCAAGAACCAGGTCAGC

CTGACCTGCCTGGTCAAAGGCTTCTACCCCAGCGACATCGCCGTGGAGTG

GGAGAGCAATGGGCAGCCGGAGAACAACTACAAGACCACGCCTCCCGTGC

TGGACTCCGACGGCTCCTTCTTCCTCTACAGCAAGCTCACCGTGGACAAG

AGCAGGTGGCAGCAGGGGAACATCTTCTCATGCTCCGTGATGCATGAGGC

TCTGCACAACCACTACACGCAGAAGAGCCTCTCCCTGTCCCCGGGTAAAT

GA

SEQ ID NO: 5: Peptide Sequence of the huFcγ4h-L-DI-IFNβ (the Signal Peptide and the K to A Substitution at the End of CH3 are Underlined; and L-DI-IFNβ in Bold)

<u>MELPVRLLVLMFWIPASLS</u>EPKSSDKTHTCPPCPAPEFLGGPSVFLFPPK

PKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTPP

-continued
```
VLDSDGSFFLYSKLTVDKSRWQQGNIFSCSVMHEALHNHYTQKSLSLSPG

AGGGGSGGGGSGGGSGMSYNLLGFLQRSSNFQSQKLLWQLNGRLEYCLKD

RMNFDIPEEIKQLQQFQKEDAAATIYEMLQNIFAIFRQDSSSTGWNETIV

ENLLANVYHQINHLKTVLEEKLEKEDFTRGKLMSSLHLKRYYGRILAYLK

AKEYSACAWTIVRVEILRNFYFINRLTGYLRN
```

SEQ ID NO: 6: DNA Sequence of the huFcγ4h-L-DI-IFNβ Chain from the Translation Initiation Codon to the Translation Stop Codon (Coding Sequence in Upper Case and Non-Coding Sequence in Lower Case)

```
ATGGAGTTGCCTGTTAGGCTGTTGGTGCTGATGTTCTGGATTCCTGgtga ggagagagggaagtgagggaggagaatggacagggagcaggagcactgaa tcccattgctcattccatgtattctggcatgggtgagaagatgggtctta tcctccagcatggggcctctggggtgaatacttgttagagggaggttcca gatgggaacatgtgctataatgaagattatgaaatggatgcctgggatgg tctaagtaatgcctagaagtgactagacacttgcaattcactttttttgg taagaagagatttttaggctataaaaaaatgttatgtaaaaataaacatc acagttgaaataaaaaaaaatataaggatgttcatgaattttgtgtataa ctatgtatttctctctcattgtttcagCTTCCTTAAGCGAGCCCAAATCT TCTGACAAAACTCACACATGCCCACCGTGCCCAGgtaagccagcccaggc ctcgccctccagctcaaggcgggacaggtgccctagagtagcctgcatcc agggacaggccccagccgggtgctgacgcatccacctccatctcttcctc agCACCTGAGTTCCTGGGGGGACCATCAGTCTTCCTGTTCCCCCCAAAAC

CCAAGGACACTCTCATGATCTCCCGGACCCCTGAGGTCACGTGCGTGGTG

GTGGACGTGAGCCAGGAAGACCCCGAGGTCCAGTTCAACTGGTACGTGGA

TGGCGTGGAGGTGCATAATGCCAAGACAAAGCCGCGGGAGGAGCAGTTCA

ACAGCACGTACCGTGTGGTCAGCGTCCTCACCGTCCTGCACCAGGACTGG

CTGAACGGCAAGGAGTACAAGTGCAAGGTCTCCAACAAAGGCCTCCCGTC

CTCCATCGAGAAAACCATCTCCAAAGCCAAAGgtgggacccacggggtgc gagggccacatggacagaggtcagctcggcccaccctctgccctgggagt gaccgctgtgccaacctctgtccctacagGGCAGCCCCGAGAGCCACAGG

TGTACACCCTGCCCCCATCCCAGGAGGAGATGACCAAGAACCAGGTCAGC

CTGACCTGCCTGGTCAAAGGCTTCTACCCCAGCGACATCGCCGTGGAGTG

GGAGAGCAATGGGCAGCCGGAGAACAACTACAAGACCACGCCTCCCGTGC

TGGACTCCGACGGCTCCTTCTTCCTCTACAGCAAGCTCACCGTGGACAAG

AGCAGGTGGCAGCAGGGGAACATCTTCTCATGCTCCGTGATGCATGAGGC

TCTGCACAACCACTACACGCAGAAGAGCCTCTCCCTGTCCCCGGGTGCAG

GGGGCGGGGCAGCGGGGCGGAGGATCCGGCGGGGCTCGGGTATGAGC

TACAACTTGCTTGGATTCCTACAAAGAAGCAGCAATTTTCAGAGTCAGAA

GCTCCTGTGGCAATTGAATGGGAGGCTTGAATATTGCCTCAAGGACAGGA

TGAACTTTGACATCCCTGAGGAGATTAAGCAGCTGCAGCAGTTCCAGAAG

GAGGACGCCGCAGCCACCATCTATGAGATGCTCCAGAACATCTTTGCTAT

TTTCAGACAAGATTCATCTAGCACTGGCTGGAATGAGACTATTGTTGAGA

ACCTCCTGGCTAATGTCTATCATCAGATAAACCATCTGAAGACAGTCCTG

GAAGAAAAACTGGAGAAGAAGATTTCACCAGGGGAAAACTCATGAGCAG

TCTGCACCTGAAAAGATATTATGGGAGGATTCTGGCCTACCTGAAGGCCA

AGGAGTACAGTGCCTGTGCCTGGACCATAGTCAGAGTGGAAATCCTAAGG

AACTTTTACTTCATTAACAGACTTACAGGTTACCTCCGAAACTGA
```

Example 2

Construction of DNA Sequences for the Expression of huFcγ4h-mono-L-DI-IFNβ Variants Containing H435A Substitution in γ4

DNA sequences for the expression of huFcγ4h-mono-L-DI-IFNβ variants containing the H435A substitution (Kabat numbering) in γ4 were constructed. These include DNA sequences encoding the heterodimers huFcγ4h(H435A)/huFcγ4h-L-DI-IFNβ, huFcγ4h/huFcγ4h(H435A)-L-DI-IFNβ and huFcγ4h(H435A)/huFcγ4h(H435A)-L-DI-IFNβ. The mutation from the CAC codon to GCG encoding the H435A substitution in the naked huFcγ4h chain or the huFcγ4h-L-DI-IFNβ fusion protein chain was introduced by overlapping PCR (Daugherty et al. (1991) *Nucleic Acids Res.* 19:2471-2476) with mutagenic primers, using forward primer 5'-G GCTCTGCACAAC GCGTACACGCAGAAGAG (SEQ ID NO: 12), where GCG encodes the alanine substitution, and reverse primer 5'-CTCTTCTGCGTGTACGCGTT GTGCAGAGCC (SEQ ID NO: 13), where CGC is the anti-codon of the alanine substitution.

Example 3

Expression of Fusion Proteins

The huFcγ4h-mono-L-DI-IFNβ heterodimer was produced in mammalian cells by coexpressing the human Fcγ4h chain and the human Fcγ4h-Linker-DI-IFNβ chain, the transcription units of which were contained in one single plasmid or two separate plasmids. For rapid analysis of protein expression, the plasmid pdCs-Fcγ4h and pdCs-Fc Fcγ4h-Linker-DI-IFNβ or variants were introduced into human kidney 293T cells (GenHunter Corporation, Nashville, Tenn.) by transient transfection using lipofectamine (Invitrogen, Carlsbad, Calif.).

Mouse myeloma NS/0 and Chinese hamster ovary cells were used to obtain stably transfected clones which express the huFcγ4h-mono-L-DI-IFNβ heterodimer. For high level expression, the plasmid pdCs containing both the human Fcγ4h chain and the human Fcγ4h-Linker-DI-IFNβ chain transcription units was introduced into the mouse myeloma NS/0 cells by electroporation. NS/0 cells were grown in Dulbecco's modified Eagle's medium supplemented with 10% heat-inactivated fetal bovine serum, 2 mM glutamine and penicillin/streptomycin. About $5 \times 10^6$ cells were washed once with PBS and resuspended in 0.5 ml PBS. 10 µg of linearized plasmid DNA were then incubated with the cells in a Gene Pulser Cuvette (0.4 cm electrode gap, BioRad) on ice for 10 min. Electroporation was performed using a Gene Pulser (BioRad, Hercules, Calif.) with settings at 0.25 V and 500 µF. Cells were allowed to recover for 10 min on ice, after which they were resuspended in growth medium and plated onto two 96 well plates. Stably transfected clones were selected by their growth in the presence of 100 nM methotrexate (MTX), which was added to the growth medium two days post-transfection. The cells were fed every 3 days for two to three more times, and MTX-resistant clones appeared in 2 to 3 weeks. Supernatants from clones were assayed by anti-Fc ELISA to identify high producers. High producing clones were isolated and propagated in growth medium containing 100 nM MTX. The growth medium typically used was H-SFM or CD medium (Invitrogen, Carlsbad, Calif.).

Figure 8:
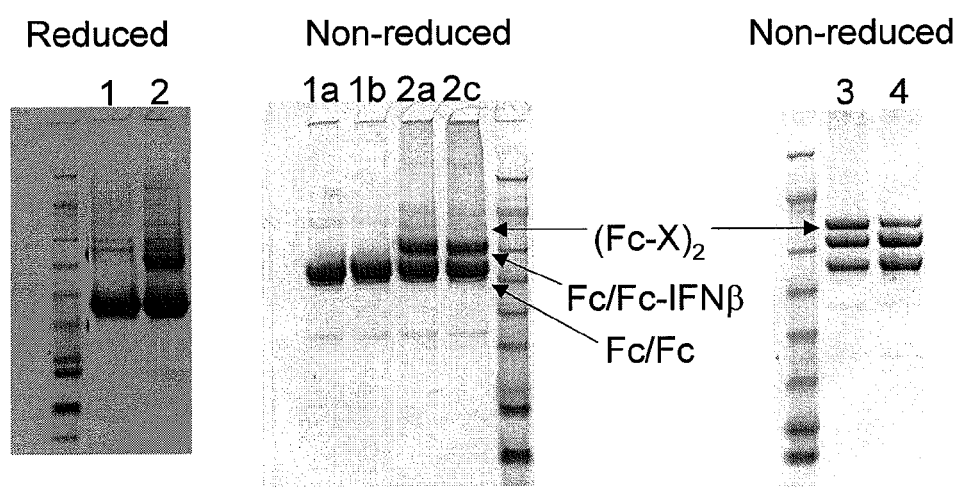
FIG. 8 shows an SDS-PAGE analysis of huFcγ4h-mono-L-DI-IFNβ produced by transient coexpression of the human Fcγ4h chain and the human Fcγ4h-Linker-DI-IFNβ chain in 293T cells under reducing (left panel) and non-reducing conditions (middle panel). In the left panel, lane 2 shows that both the Fcγ4h chain and the Fcγ4h-Linker-DI-IFNβ chain were expressed, while lane 1 is a control showing the expression of Fcγ4h alone. In the middle panel, the transient coexpression of the human Fcγ4h chain and the human Fcγ4h-Linker-DI-IFNβ chain was analyzed under non-reducing conditions. Duplicate samples of the Fcγ4h chain (the two lanes labeled 1a and 1b) or the coexpression of the Fcγ4h chain and the Fcγ4h-Linker-DI-IFNβ chain (the two lanes labeled 2a and 2c) were analyzed. The right panel shows that coexpression of Fc and Fc-IL-2 chains from two stably transfected clones (the two lanes labeled 3 and 4) gave the normal and expected ratio of naked Fc homodimer:Fc/Fc-IL2 heterodimer:Fc-IL2 homodimer on SDS-PAGE under non-reducing conditions.
Figure 9:
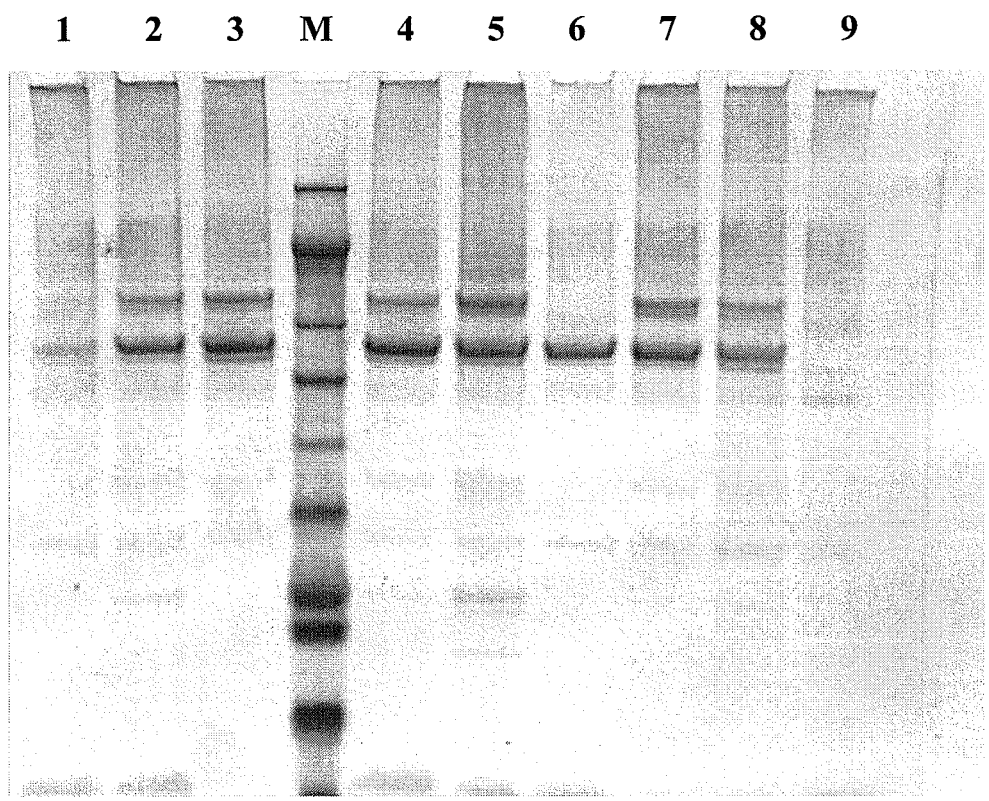
FIG. 9 shows an SDS-PAGE analysis of conditioned media from a number of stable NS0 clones coexpressing the Fcγ4h chain and the Fcγ4h-Linker-DI-IFNβ chain under non-reducing conditions. All the clones produced the Fcγ4h homodimer and Fcγ4h/Fcγ4h-IFNβ heterodimer, but little or no Fcγ4h-IFNβ homodimer.

For routine characterization by gel electrophoresis, the huFc-IFNβ fusion protein secreted into the medium was captured on Protein A Sepharose beads (Repligen, Cambridge, Mass.) and then eluted by boiling the sample in protein sample buffer, with or without a reducing agent such as β-mercaptoethanol. The samples were analyzed by SDS-PAGE (sodium dodecyl sulfate-polyacrylamide gel electrophoresis) and the protein bands were visualized by Coomassie staining. FIG. 8 shows the huFcγ4h-mono-L-DI-IFNβ produced by transient coexpression of human Fcγ4h chain and the human Fcγ4h-Linker-DI-IFNβ in 293T cells. Lane 2 of the SDS-PAGE analysis under reducing conditions (left panel) shows that both the Fcγ4h chain and the Fcγ4h-Linker-DI-IFNβ chain were expressed, and the naked Fc was expressed at a higher level than the fusion protein. When these two chains were coexpressed at these levels, one would expect that the non-reduced gel should show a ratio of naked Fc homodimer:Fc/Fc-IFNβ heterodimer:Fc-IFNβ homodimer according to the binomial $a^2+2ab+b^2$, where a and b are the relative expression levels of the naked Fc chain and the fusion protein chain, respectively, as seen on the reduced gel. Surprisingly, SDS-PAGE analysis under non-reducing conditions (middle panel) shows that very little Fc-IFNβ homodimer ("(Fc-X)$_2$") was produced, in sharp contrast to the more normal pattern (ratio according to $a^2+2ab+b^2$) that was obtained with coexpression of Fc and Fc-IL-2 analyzed also under non-reducing conditions (right panel). Stable clones coexpressing the Fcγ4h chain and the Fcγ4h-Linker-DI-IFNβ chain had a similar lack of the Fc-IFNβ homodimer (FIG. 9), suggesting that the production of the Fc-IFNβ homodimer in the cell is unfavorable, probably due to protein folding since IFNβ itself tends to aggregate.

Example 4

Purification of huFcγ4h-mono-L-DI-IFNβ

Purification of Fc-containing fusion proteins was performed based on the affinity of the Fc protein moiety for Protein A. Briefly, cell supernatant containing the fusion protein was loaded onto a pre-equilibrated Protein A Sepharose column and the column was washed extensively in same buffer (150 mM sodium phosphate, 100 mM NaCl at neutral pH). Bound protein was eluted at a low pH (pH 2.5-3) in the same buffer and eluate fractions were immediately neutralized. The huFcγ4h-mono-L-DI-IFNβ heterodimer could be readily separated from the Fcγ4h homodimer based on the affinity of IFNβ protein for Cibacron Blue 3GA (Blue Sepharose Fast Flow column; Pharmacia). Culture supernatant containing the expressed fusion protein was adjusted to 1 M NaCl and loaded onto the Blue Sepharose Fast Flow column which had been pre-equilibrated with Buffer A (Buffer A: 20 mM Sodium Phosphate (pH 7.2) 1 M NaCl). The column was washed with 10 column volumes of Buffer A, followed by 15 column volumes of a 1:1 mixture of Buffer A:Buffer B (Buffer B: 20 mM Sodium Phosphate (pH 7.2), 50% (v/v) Ethylene Glycol). The heterodimer was eluted in 100% Buffer B and 1 ml fractions were collected into tubes containing 0.5 ml Buffer A. The purified huFcγ4h-mono-L-DI-IFNβ was analyzed by size exclusion chromatography (SEC) and further confirmed by a Western blot probed with an anti-IFNβ antibody.

Example 5

Expression of Immunoglobulin- and huFc-Mono-Ligand Variants Containing Single Substitution that Abrogates FcRn Binding A huFc-mono-L-DI-IFNβ variant derived from an Fc-SEED (see WO2007/110205) was produced in the form of huFc-AG2(H435A)/huFc-GA2-L-DI-IFNβ. Additional variants that were produced include IgG subclass and ligand variants, such as huFcγ1(H435A)/huFcγ1-IL2 and deimmunized KS-γ1(H435A)/KS-γ1-IL2, a class of whole IgG fusion proteins known as immunocytokines (Davis et al. (2003) *Cancer Immunol. Immunother.* 52:297-308).

In addition to H435, H310 was also reported to be involved in FcRn binding (Kim et al. (1999) *Eur. J. Immunol.* 29:2819-2825). Hence another huFcγ4h-mono-L-DI-IFNβ variant containing the H310A substitution was produced in the form of a huFcγ4h(H310A)/huFcγ4h-L-DI-IFNβ heterodimer.

Example 6

Activity of huFc-IFNβ Proteins in Cell-Based Bioassays

Figure 10:
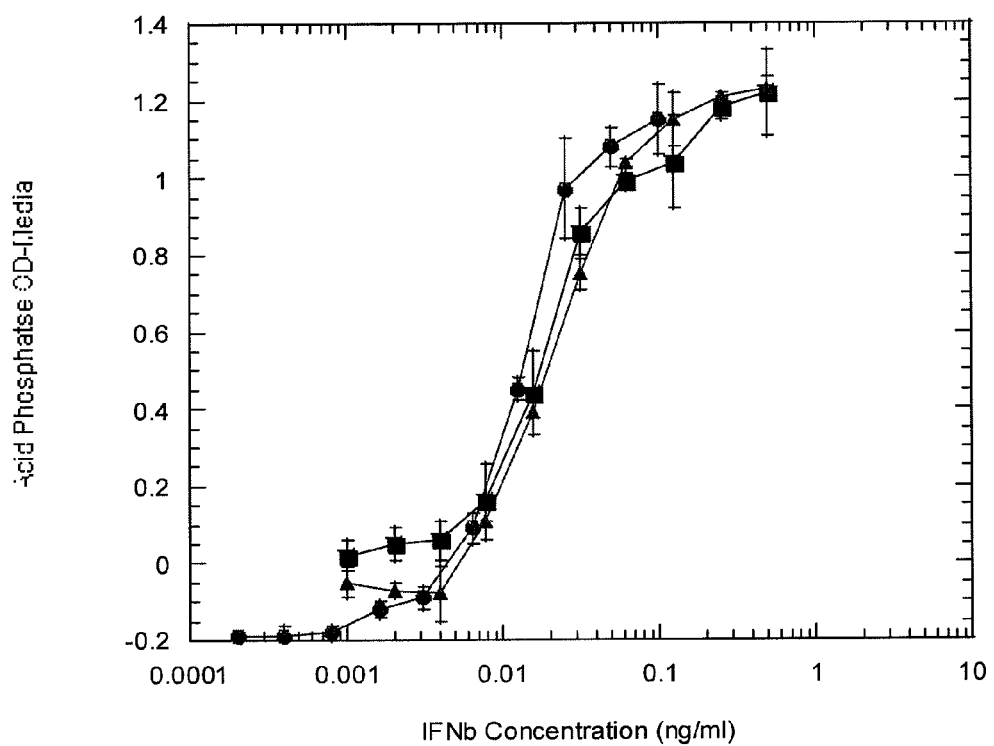
FIG. 10 shows the biological activities of purified Fcγ4h-mono-L-DI-IFNβ (squares) and Fcγ4h-mono-L-DI-IFNβ variant containing the H435A substitution (triangles) in a cytopathic effect (CPE) inhibition assay. The human epithelial lung carcinoma line A549 was used as a host for the encephalomyocarditis virus (EMCV). Rebif (circles) was used as the positive control.

The activity of the Fc-IFNβ fusion proteins was determined in an antiviral assay. Viral replication is often toxic to cells, resulting in cell lysis, an effect known as a cytopathic effect (CPE). Interferons act on pathways that inhibit viral proliferation, protecting cells from CPE. The antiviral activity of IFNβ could be assayed by measuring the extent to which CPE is reduced (CPER), as described in "*Lymphokines and Interferons: A Practical Approach*," edited by M. J. Clemens, A. G. Morris, and A. J. H. Gearin, I.R.L. Press, Oxford, 1987. The antiviral activities of purified Fcγ4h-mono-L-DI-IFNβ and Fcγ4h-mono-L-DI-IFNβ variant containing the H435A substitution were compared to Rebif using the human epithelial lung carcinoma line A549 (ATCC # CCL-185) as a host for the encephalomyocarditis virus (EMCV; ATCC # VR 129B). The effective dose (ED50) was set as the amount of protein that led to 50% CPER (i.e. 50% of the cells are protected), determined relative to uninfected control cells. On a molar basis, both Fcγ4h-mono-L-DI-IFNβ and Fcγ4h-mono-L-DI-IFNβ variant were found to be at least as potent as Rebif in this CPE assay (FIG. 10).

Example 7

Pharmacokinetics of huFc-IFNβ Proteins

The pharmacokinetics (PK) of huFc-IFNβ heterodimeric fusion proteins and variants were determined in Balb/c mice (n=3). For intravenous administration, 25 µg of the heterodimeric fusion protein were injected into the tail vein of each mouse. Blood was collected into heparin-coated tubes immediately following injection (t=0 min), and at 30 min, 1 hr, 2 hrs, 4 hrs, 8 hrs, 24 hrs, 48 hrs, 72 hrs and 96 hrs post-injection by retro-orbital bleeding. For subcutaneous administration, 50 µg of the heterodimeric fusion protein were injected per mouse. Blood was collected into heparin-coated tubes 1, 2, 4, 8, 24, 48, 72 and 96 hrs post-injection by retro-orbital bleeding. Cells were removed by centrifugation (4 min at 12,500 g) and the concentration of the fusion protein in the plasma was determined by an anti-huFc ELISA consisting of an anti-(H&L) (AffiniPure Goat anti-Human IgG (H+L), Jackson Immuno Research Laboratories, West Grove, Pa.) capture and anti-Fc (HRP-conjugated (Fab')$_2$ dimer goat anti-human IgG Fc, Jackson Immuno Research Laboratories, West Grove, Pa.) detection, and an anti-huFc-IFNβ ELISA consisting of an anti-(H&L) capture and anti-huIFNβ (Goat anti-human IFN-β Biotinylated, R&D Systems, Minneapolis, Minn.) detection. Furthermore, the integrity of the circulating fusion protein was confirmed by an immunoblot of the PK serum samples probed with an anti-huFc antibody or an anti-huIFNβ antibody.

Figure 11:
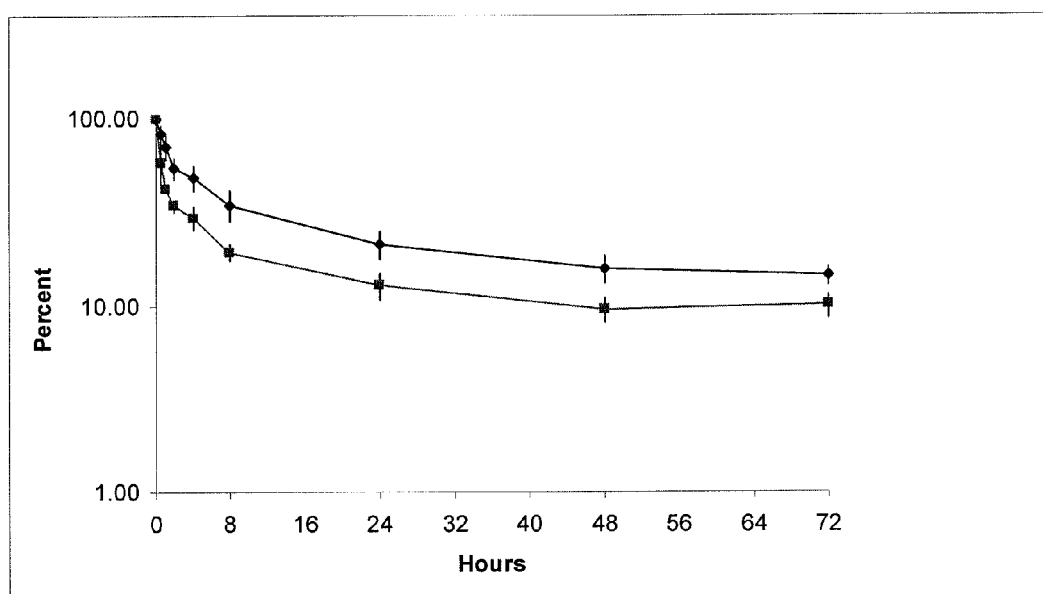
FIG. 11 compares the pharmacokinetic profiles of intravenously administered huFcγ4h-mono-L-DI-IFNβ (diamonds) and huFcγ4h-mono-L-DI-IFNβ variant containing the H435A substitution in the form of the huFcγ4h(H435A)/huFcγ4h-L-DI-IFNβ heterodimer (squares). Mice (n=3) were injected intravenously with 25 μg of total protein/mouse. Serum concentrations of the injected protein at different time points were determined by anti-hu Fc ELISA.
Figure 12:
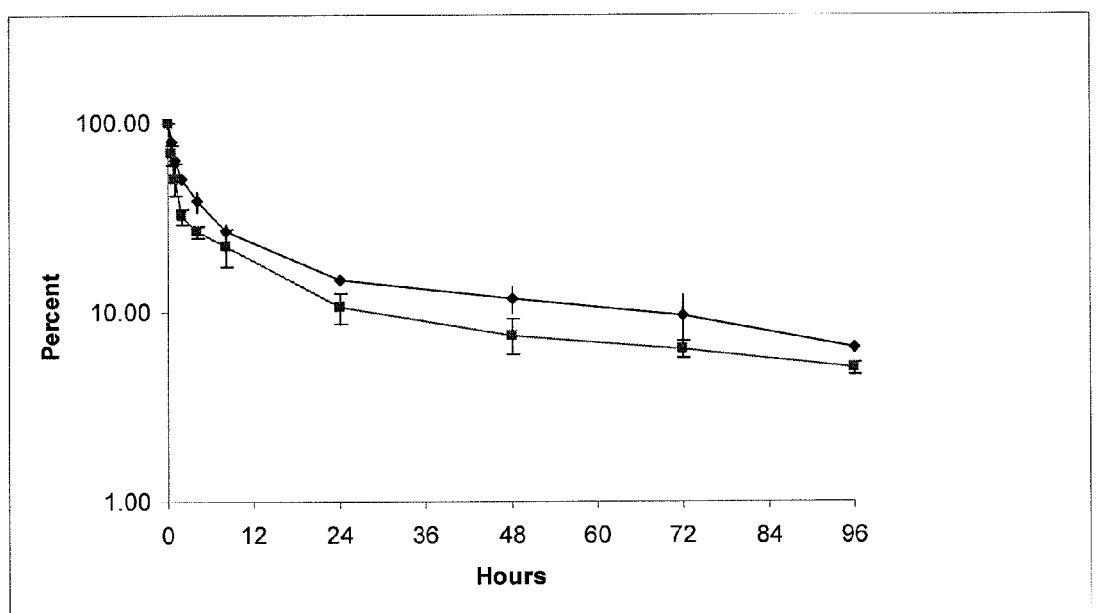
FIG. 12 compares the pharmacokinetic profiles of intravenously administered huFcγ4h-mono-L-DI-IFNβ (diamonds) and huFcγ4h-mono-L-DI-IFNβ variant containing the H435A substitution in the form of the huFcγ4h(H435A)/huFcγ4h-L-DI-IFNβ heterodimer (squares). Mice (n=3) were injected intravenously with 25 μg of total protein/mouse. Serum concentrations of the injected protein at different time points were determined by an ELISA consisting of anti-hu (H&L) capture and anti-hu IFNβ detection.
Figure 13:
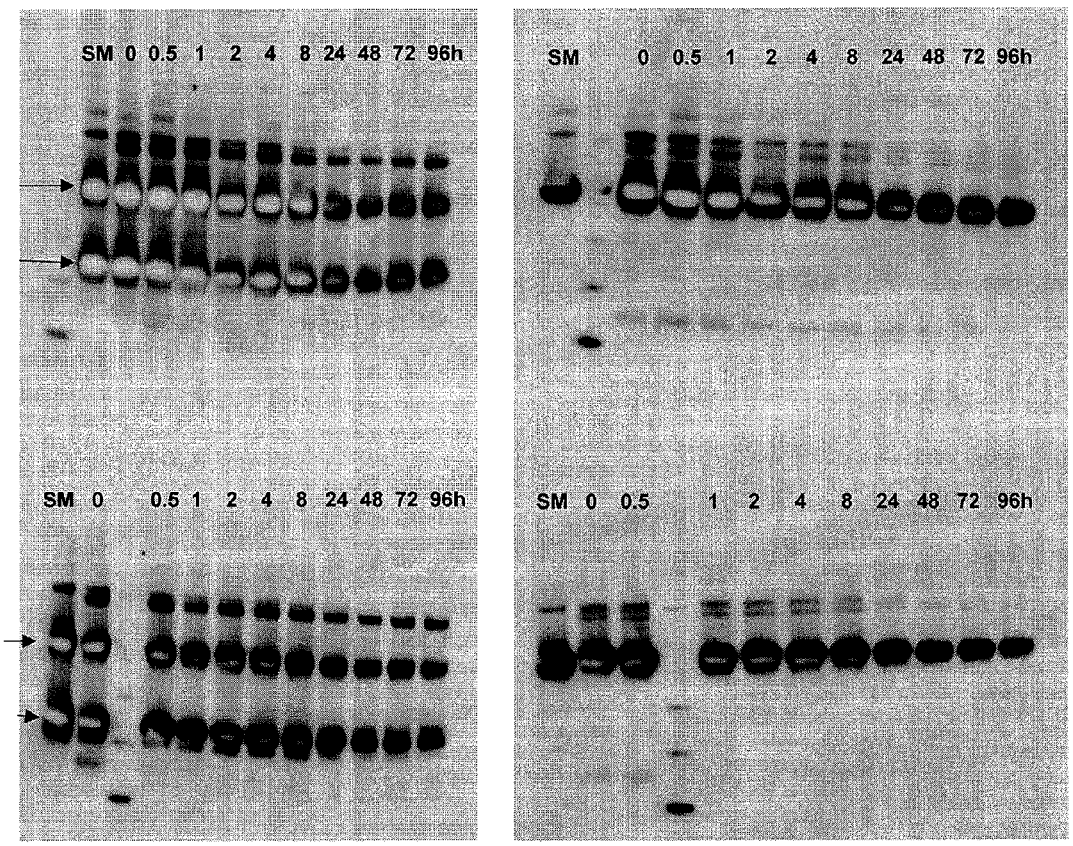
FIG. 13 is a Western blot analysis of the mouse serum samples from the intravenous pharmacokinetics studies under reducing conditions. Top left: huFcγ4h-mono-L-DI- IFNβ probed with anti-hu Fc; bottom left: huFcγ4h-mono-L-DI-IFNβ variant containing the H435A substitution probed with anti-hu Fc; top right: huFcγ4h-mono-L-DI-IFNβ probed with anti-hu IFNβ; bottom right: huFcγ4h-mono-L-DI-IFNβ variant containing the H435A substitution probed with anti-hu IFNβ.

FIGS. 11 and 12 compare the pharmacokinetic profiles of intravenously administered huFcγ4h-mono-L-DI-IFNβ and an huFcγ4h-mono-L-DI-IFNβ variant containing the H435A substitution in the form of the huFcγ4h(H435A)/huFcγ4h-L-DI-IFNβ heterodimer, as determined by anti-huFc ELISA and anti-huFc-IFNβ ELISA, respectively. The huFcγ4h-mono-L-DI-IFNβ has a circulating half-life of 48 hr, which is many times longer than that of IFNβ, which was in minutes. Surprisingly, the huFcγ4h-mono-L-DI-IFNβ variant containing the H435A substitution has a circulating half-life of 46 hr, which is essentially identical to that of huFcγ4h-mono-L-DI-IFNβ, within experimental error. The H435A variant also has an AUC (area under the curve) about two-thirds of that of the wild-type, which is several hundred times that of IFNβ. The anti-huFc-IFNβ ELISA detected specifically the fusion protein and not any cleaved fragments without the N-terminal Fc or C-terminal IFNβ moieties. Furthermore, Western blot analyses of the intravenous PK samples under reducing conditions using either anti-huFc antibody or anti-huIFβ antibody as probes confirmed that the fusion proteins stayed intact in vivo (FIG. 13). In the top left section of FIG. 13, the upper arrow denotes the huFcγ4h-L-DI-IFNβ polypeptide chain, and the bottom arrow denotes the huFcγ4h chain. Similarly, in the bottom left section of FIG. 13, the upper arrow denotes the huFcγ4h-L-DI-IFNβ polypeptide chain, and the bottom arrow denotes the huFcγ4h(H435A) chain.

Figure 14:
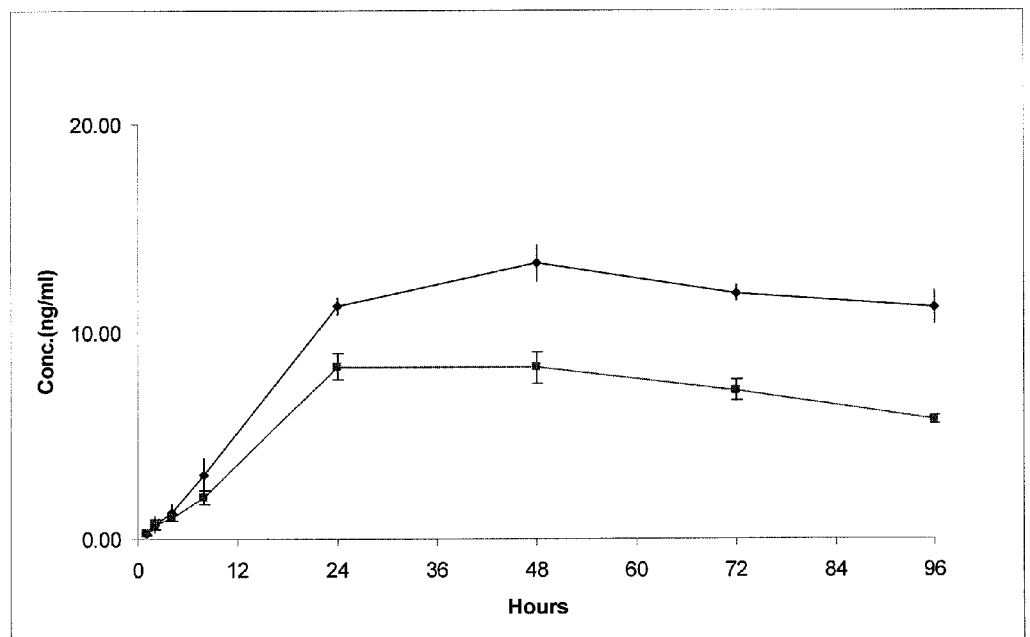
FIG. 14 compares the pharmacokinetic profiles of subcutaneously administered huFcγ4h-mono-L-DI-IFNβ (diamonds) and huFcγ4h-mono-L-DI-IFNβ variant containing the H435A substitution in the form of the huFcγ4h(H435A)/huFcγ4h-L-DI-IFNβ heterodimer (squares). Mice (n=3) were injected subcutaneously with 50 μg of total protein/mouse. Serum concentrations of the injected protein at different time points were determined by anti-hu Fc ELISA.
Figure 15:
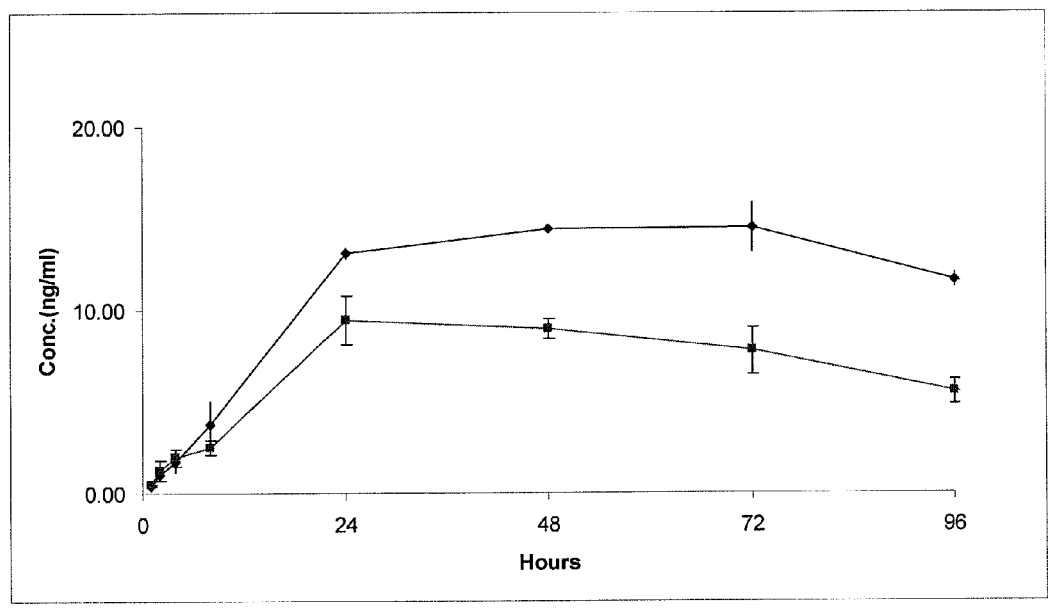
FIG. 15 compares the pharmacokinetic profiles of subcutaneously administered huFcγ4h-mono-L-DI-IFNβ (diamonds) and huFcγ4h-mono-L-DI-IFNβ variant containing the H435A substitution in the form of the huFcγ4h(H435A)/huFcγ4h-L-DI-IFNβ heterodimer (squares). Mice (n=3) were injected subcutaneously with 50 μg of total protein/mouse. Serum concentrations of the injected protein at different time points were determined by an ELISA consisting of anti-hu (H&L) capture and anti-hu IFNβ detection.
Figure 16:
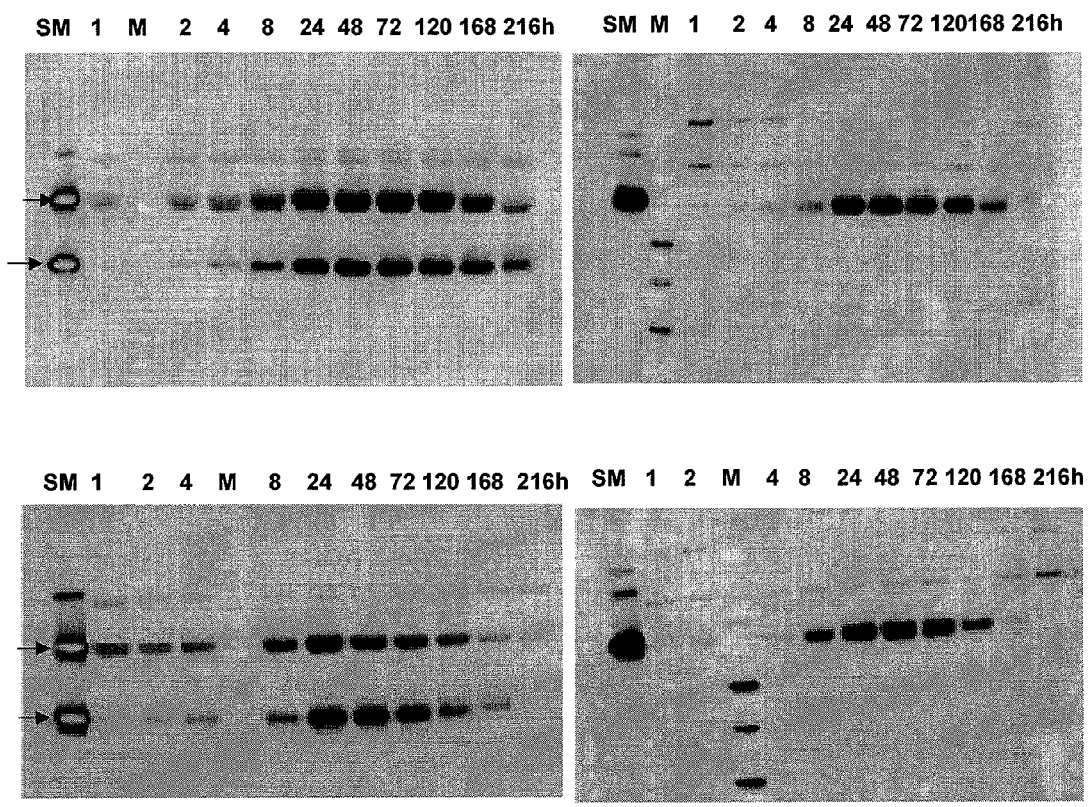
FIG. 16 is a Western blot analysis of the mouse serum samples from the subcutaneous pharmacokinetics studies under reducing conditions. Top left: huFcγ4h-mono-L-DI-IFNβ probed with anti-hu Fc; bottom left: huFcγ4h-mono-L-DI-IFNβ variant containing the H435A substitution probed with anti-hu Fc; top right: huFcγ4h-mono-L-DI-IFNβ probed with anti-hu IFNβ; bottom right: huFcγ4h-mono-L-DI-IFNβ variant containing the H435A substitution probed with anti-hu IFNβ.

FIGS. 14 and 15 compare the pharmacokinetic profiles of the same two molecules administered subcutaneously. The huFcγ4h-mono-L-DI-IFNβ and the huFcγ4h-mono-L-DI-IFNβ variant containing the H435A substitution have a similar circulating half-life, which is many times longer than that of IFNβ. Surprisingly, the huFcγ4h-mono-L-DI-IFNβ variant containing the H435A substitution has a circulating half-life of 46 hr, which is essentially identical to that of huFcγ4h-mono-L-DI-IFNβ, within experimental error. The H435A variant also has an AUC (area under the curve) about two-thirds of that of the wild-type, which is several hundred times that of IFNβ. The anti-hu Fc ELISA and anti-hu IFNβ ELISA detected the two ends of the fusion protein molecule. Furthermore, Western blot analyses of the subcutaneous PK samples under reducing conditions using either anti-hu Fc antibody or anti-hu IFNβ antibody as probes confirmed that the fusion proteins stayed intact in vivo (FIG. 16). In the top left panel of FIG. 16, the upper arrow denotes the huFcγ4h-L-DI-IFNβ polypeptide chain, and the bottom arrow denotes the huFcγ4h chain. Similarly, in the bottom left panel of FIG. 16, the upper arrow denotes the huFcγ4h-L-DI-IFNβ polypeptide chain, and the bottom arrow denotes the huFcγ4h(H435A) chain.

Example 8

Reduced Immunogenicity of Immunoglobulin- and huFc-Mono-Ligand Variants Containing Single Substitution that Abrogates FcRn Binding To demonstrate the reduced immunogenicity of immunoglobulin- or huFc-mono-ligand variants containing a single substitution that abrogates FcRn binding of only one polypeptide chain, mice were immunized with huFcγ4h-mono-L-DI-IFNβ or huFcγ4h-mono-L-DI-IFNβ variant containing the H435A mutation. Antibody titers were compared at appropriate times after immunization.

Two groups of female, 8-weeks-old Balb/C mice (5 mice per group) were injected subcutaneously with 33 µg/mouse of huFcγ4h-mono-L-DI-IFNβ or huFcγ4h-mono-L-DI-IFNβ variant containing the H435A mutation, respectively. On day 15, mice received a subcutaneous boost injection of 33 µg/mouse of huFcγ4h-mono-L-DI-IFNβ or huFcγ4h-mono-L-DI-IFNβ variant containing the H435A mutation. Mouse antibody titers were determined on Day 26 by ELISA. This consisted of coating the wells of a 96-well plate with 1 µg of goat anti-mouse IgG (H+L) (Jackson ImmunoResearch Laboratories, West Grove, Pa., cat #115-005-062) by incubation overnight at 4° C. in PBS followed by washing four times with PBS 0.05% Tween. Next, the goat anti-mouse IgG (H+L)-coated plate was blocked with 1% milk, washed four times with PBS 0.05% Tween, dried, and stored at −20° C. For capturing mouse antibodies, serum was initially diluted 1:1000 followed by serial dilutions of 1:2 in PBS 0.05% Tween and added to the goat anti-mouse IgG (H+L)-coated wells for one hour at 37° C. The wells were then washed four times with PBS 0.05% Tween. The captured antibodies were detected by adding the immunogens, huFcγ4h-mono-L-DI-IFNβ or huFcγ4h-mono-L-DI-IFNβ variant containing the H435A mutation at 0.5 µg/ml, and a 1:20,000 dilution of F(ab)$_2$ Goat anti-hu-IgG-Fc-HRP (Jackson ImmunoResearch Laboratories, cat #109-036-098) in PBS 0.05% Tween. The plate was incubated for one hour at room temperature followed by four washes with PBS 0.05% Tween. Signal detection was carried out using 100 µl of 3',3',5',5'-Tetramethylbenzidine (TMB), and after 15 minutes, the reaction was stopped with 100 µl of 2N H$_2$SO$_4$.

Figure 17:
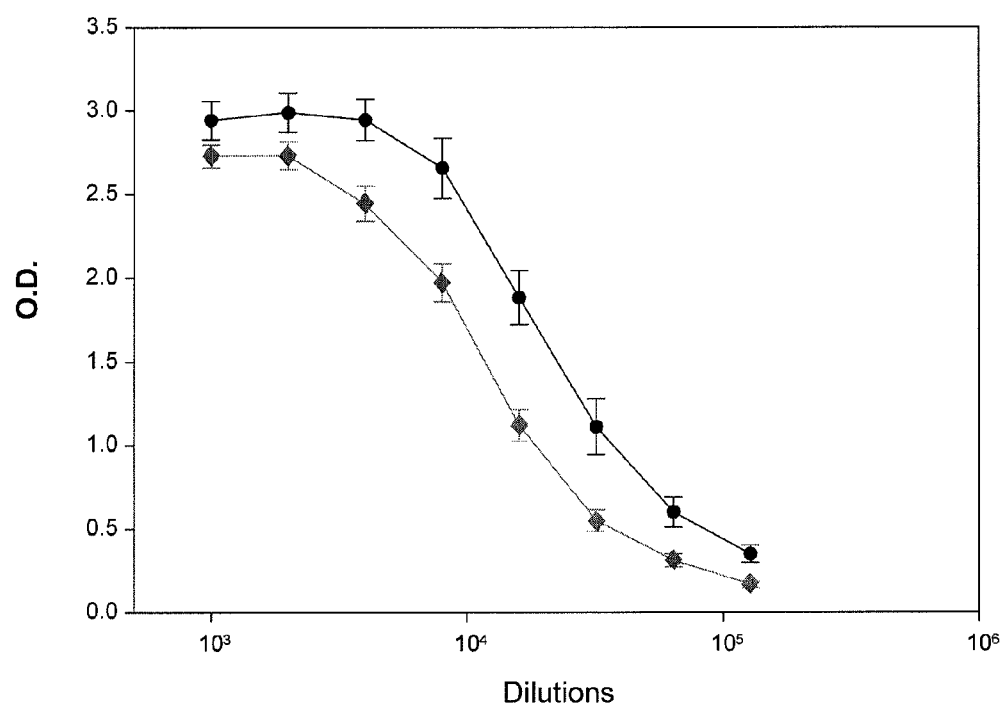
FIG. 17 compares the antibody titers of mice that were immunized with huFcγ4h-mono-L-DI-IFNβ (circles) or huFcγ4h-mono-L-DI-IFNβ variant containing the H435A substitution (diamonds) following boost injections. Mouse antibody titers were determined by ELISA.

FIG. 17 compares the antibody titers of mice that were immunized with huFcγ4h-mono-L-DI-IFNβ or huFcγ4h-mono-L-DI-IFNβ variant containing the H435A mutation. Mice that received the huFcγ4h-mono-L-DI-IFNβ variant containing the H435A mutation (diamonds) had lower titer than mice immunized with huFcγ4h-mono-L-DI-IFNβ (circles) indicating that that the variant had reduced immunogenicity. The comparison between groups was analyzed by Sigma-Plot using Paired-t-test. The difference between two groups was statistically significant (Normality test: p=0.288, t=5.422 with 7 degrees of freedom (p=<0.001)).

Example 9

Determining Immunogenicity by In Vitro T Cell Assay

To show that the huFc-mono-ligand variant containing the H435A mutation is less immunogenic than the wild-type counterpart, we use a human T cell proliferation assay that involves culturing and maturation of monocyte derived dendritic cells (DC), loading and presentation of antigen on DC, and determination of antigen-induced response in CD4+ T cells. Human peripheral blood mononuclear cells (PBMC) from healthy donors serve as a source of DC and autologous T cells. Typically PBMC are isolated by Ficoll-Hypaque gradient from leukopack samples and monocytes are purified using MACS CD14 isolation kit (Miltenyi Biotec Inc. Auburn, Calif.) and cultured with GM-CSF and IL-4 for 5 days. Immature DC are loaded with the different antigens, such as huFcγ4h-mono-L-DI-IFNβ, the huFcγ4h-mono-L-DI-IFNβ variant containing the H435A mutation, as well as tetanus toxoid. Since IFNβ has a very potent immunosuppressive effect, the huFcγ4h-mono-L-DI-IFNβ and the huFcγ4h-mono-L-DI-IFNβ variant have to be heat treated at a moderately high temperature so that the more heat-sensitive IFNβ moiety is inactivated while the more heat stable Fc remains in its native form. A useful temperature range for this selective inactivation is from 56° C. to 65° C. Alternatively, fusion proteins containing inactive IFNβ moiety can be produced recombinantly through amino acid substitutions.

After the DC are incubated with the antigens for 24 hours, they are stimulated for 24 hours with TNF-α, IL-1β, IL-6, and PGE2 to induce DC maturation. Autologous CD4+ T cells that are prepared from the same human PBMC using MACS CD4 isolation kit (Miltenyi Biotec Inc. Auburn, Calif.) are labeled with carboxyfluorescein diacetate and succinimidyl ester (CFSE) using CellTrace CFSE Proliferation Kit (Invitrogen). DC and T cells are then co-cultured for 6-7 days, after which the percentage of dividing T cells are determined on FACS. Autologous T cell proliferation stimulated by the DC-presented peptides from the huFcγ4h-mono-L-DI-IFNβ variant are expected to be lower than those against the corresponding wild-type Fc fusion protein.

What is claimed is:

1. A protein comprising two polypeptide chains, wherein the first polypeptide chain comprises native mature human interferon-β and at least a portion of an IgG constant region, the second polypeptide chain comprises at least a portion of an IgG constant region, and one of the polypeptide chains comprises a substitution corresponding to position 435 in the IgG FcRn binding site, wherein the substitution is H435A.

2. The protein of claim 1, wherein the human interferon-β is linked to the amino-terminus of the immunoglobulin constant region.

3. The protein of claim 1, wherein the human interferon-β is linked to the carboxy-terminus of the immunoglobulin constant region.

4. The protein of claim 1, wherein the second polypeptide chain comprises a biologically active molecule.

5. The protein of claim 1, wherein at least the first or second polypeptide chain comprises an antibody variable domain.

6. The protein of claim 1, wherein the portion of the IgG is an Fc fragment.

7. The protein of claim 1, wherein the IgG is IgG1, IgG2, IgG3, or IgG4.

8. A protein comprising two polypeptide chains, wherein the first polypeptide chain comprises wild-type native mature human interferon-β having one or more mutations selected from the group consisting of C17S, C17A, C17V, C17M, F50H, L57A, L130A, H131A, K136A, H140A, and H140T and at least a portion of an IgG constant region, the second polypeptide chain comprises at least a portion of an IgG constant region, and one of the polypeptide chains comprises a substitution corresponding to position 435 in the IgG FcRn binding site, wherein the substitution is H435A.

9. A pharmaceutical composition comprising the protein of claim 1 and a pharmaceutically acceptable carrier.

* * * * *